(12) United States Patent
Kennedy-Darling et al.

(10) Patent No.: US 11,994,452 B2
(45) Date of Patent: May 28, 2024

(54) MULTIPLEXED TISSUE IMAGING

(71) Applicant: Akoya Biosciences, Inc., Menlo Park, CA (US)

(72) Inventors: Julia Kennedy-Darling, Redwood City, CA (US); Peter J. Miller, Cambridge, MA (US); Peter Harvey, Wilmington, MA (US)

(73) Assignee: Akoya Biosciences, Inc., Menlo Park, CA (US)

( * ) Notice: Subject to any disclaimer, the term of this patent is extended or adjusted under 35 U.S.C. 154(b) by 511 days.

(21) Appl. No.: 16/902,215

(22) Filed: Jun. 15, 2020

(65) Prior Publication Data

US 2020/0393343 A1     Dec. 17, 2020

Related U.S. Application Data

(60) Provisional application No. 62/861,991, filed on Jun. 14, 2019.

(51) Int. Cl.
    *G01N 1/00*     (2006.01)
    *G01N 1/31*     (2006.01)
    *G01N 35/00*     (2006.01)

(52) U.S. Cl.
    CPC ....... *G01N 1/312* (2013.01); *G01N 35/00029* (2013.01); *G01N 2035/00039* (2013.01)

(58) Field of Classification Search
    CPC ............. G01N 1/312; G01N 35/00029; G01N 2035/00039
See application file for complete search history.

(56) References Cited

U.S. PATENT DOCUMENTS

| | | | | |
|---|---|---|---|---|
| 2009/0253163 A1* | 10/2009 | Xie | .................. | G01N 1/312 |
| | | | | 435/40.5 |
| 2012/0135449 A1* | 5/2012 | Xie | .................. | G01N 1/312 |
| | | | | 435/29 |

(Continued)

FOREIGN PATENT DOCUMENTS

| | | | |
|---|---|---|---|
| WO | WO 2019/152391 | 8/2019 | ............. C07K 16/00 |

OTHER PUBLICATIONS

Cappi, G., et al., "Ultra-fast and automated immunohistofluorescent multistaining using a microfluidic tissue processor", Scientific Reports, vol. 9, No. 1, (Mar. 14, 2019) (Year: 2019).*

(Continued)

*Primary Examiner* — Jamel E Williams
(74) *Attorney, Agent, or Firm* — Fish & Richardson P.C.

(57) ABSTRACT

An apparatus attaches to a microscope slide to form an enclosed fluidic chamber with input and output ports, where a tissue or cell sample on the slide can be processed using techniques such as immunohistochemical staining. Flow of reagents within the chamber can be laminar and highly uniform across the sample surface to achieve staining that is free of gradients. The sample can be imaged prior to, during, or after any given processing step. Methods for staining and imaging a sample can be implemented through one or more rounds of labeling, label removal or erasure and imaging. Samples can be imaged many times to achieve very high multiplexing levels. Samples can be placed on an imaging apparatus at various times and removed from the imaging apparatus for certain steps.

35 Claims, 12 Drawing Sheets

(56) References Cited

U.S. PATENT DOCUMENTS

2012/0135458 A1    5/2012    Corwin et al.
2015/0185453 A1    7/2015    Corwin et al.
2017/0052175 A1*  2/2017    Healy .............. G01N 35/00029

OTHER PUBLICATIONS

International Search Report and Written Opinion of the International Searching Authority for International Application No. PCT/US2020/037821, dated Jan. 18, 2021.

Akturk, G., et al., "Multiplexed Immunohistochemical Consecutive Staining on Single Slide (MICSSS): Multiplexed Chromogenic IHC Assay for High-Dimensional Tissue Analysis", Biomarkers for Immunotherapy of Cancer, pp. 497-519 (Sep. 10, 2019).

Cappi, G., et al., "Ultra-fast and automated immunohistofluorescent multistaining using a microfluidic tissue processor", *Scientific Reports*, vol. 9, No. 1, (Mar. 14, 2019).

Kim, M., et al., "Breast Cancer Diagnosis Using a Microfluidic Multiplexed Immuno histochemistry Platform", *Plus One*, vol. 5, No. 5, (May 3, 2010).

Remark, R., et al., "In-depth tissue profiling using multiplexed immunohistochemical consecutive staining on single slide", *Science Immunology*, vol. 1, pp. 1-11 (Jul. 14, 2016).

JP Office Action in Japanese Appln. No. 2021-574311, mailed on Feb. 19, 2024, 9 pages (with English translation).

\* cited by examiner

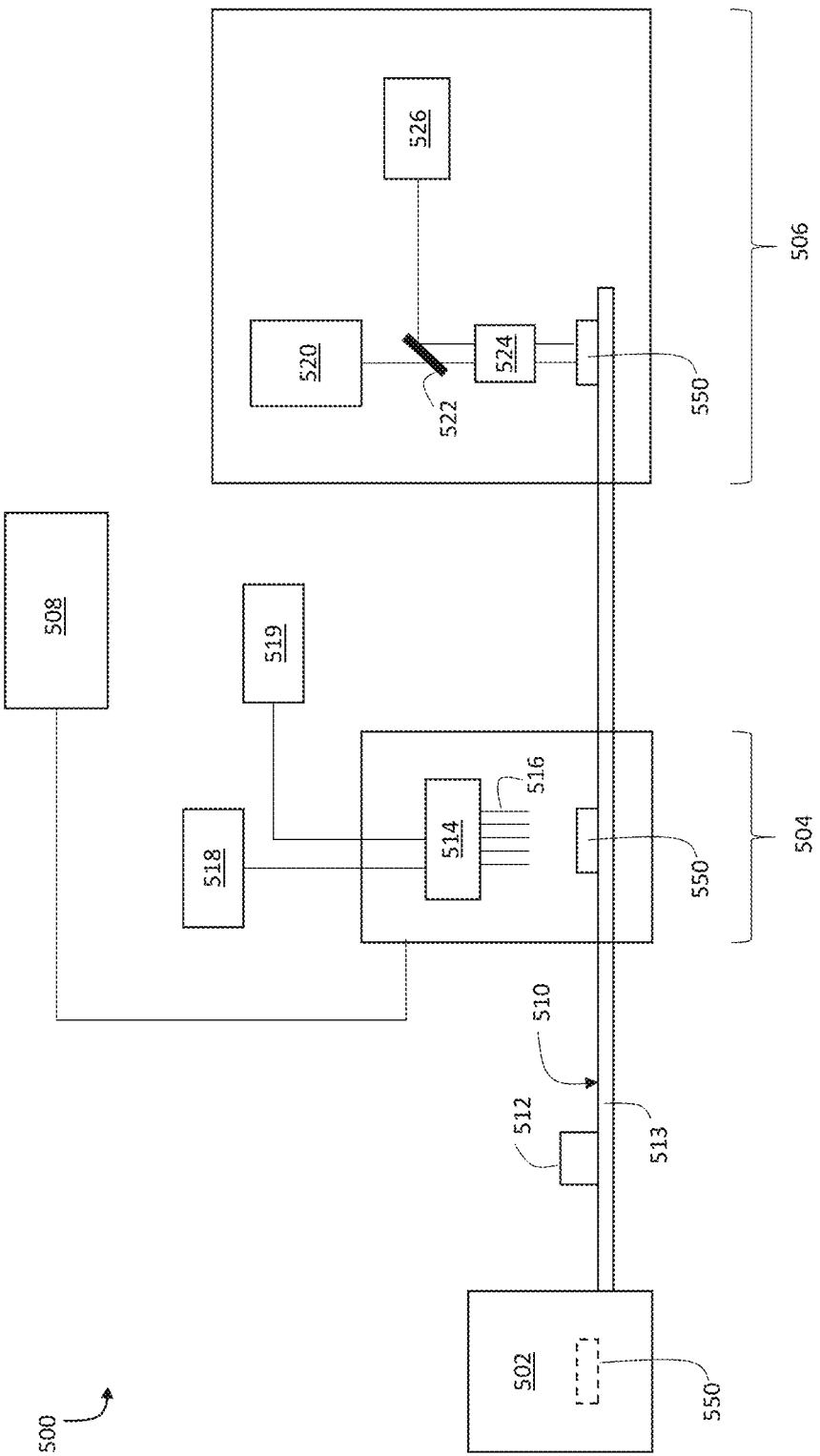

MULTIPLEXED TISSUE IMAGING

CROSS-REFERENCE TO RELATED APPLICATIONS

This application claims priority to U.S. Provisional Patent Application No. 62/861,991, filed on Jun. 14, 2019, the entire contents of which are incorporated herein by reference.

TECHNICAL FIELD

This disclosure relates systems and methods for imaging of biological samples.

BACKGROUND

Immunohistochemistry (IHC) is used to detect molecular targets of interest in cells and tissue, using antibodies to bind with specific targets of interest, and a labeling system that enables detection of the antibodies. A wide range of optical labeling systems have been devised, including colored dyes and precipitates, fluorescent molecules, and various nanoparticles. IHC is of great value in studying, diagnosing, and guiding the treatment of, a wide range of diseases.

To understand certain biological or medical processes, it can be vital to know the amount, or presence, of several molecular species in each cell. This is because the role or function of a given cellular population is not readily determined by imaging any one molecular species. Multiplex IHC techniques have been developed that can detect or quantify more than one molecular target, including targets that are localized within the same compartment of a given cell.

SUMMARY

The disclosure features methods and systems for multiplex imaging of biological samples. The methods can include, for example, forming an enclosed chamber around a sample on a substrate such as a microscope slide. The chamber has a relatively small volume, and reagents can be introduced into the chamber to perform multiple labeling and imaging cycles on the sample. During each cycle, the sample can be labeled with one or more probes and one or more images of the probes can be obtained. The probes can subsequently be removed and additional probes can be bound to the sample and images. Each type of probe typically binds selectively to one type of component in a sample (e.g., one type of protein marker, for example), and the corresponding image of that type of probe yields quantitative information about the distribution and quantity of the component in the sample. By performing repeated cycles of labeling and imaging, a relatively large number (e.g., 20 or more, 40 or more, or even more) of different sample components can be imaged and quantified.

By enclosing the sample within a chamber of relatively small volume, the quantity of probes and capture agents used to detect sample components can be relatively small, and the time duration of labeling and imaging cycles can be maintained at manageable levels, an important consideration for highly multiplexed analyses. Further, the relatively small chamber volumes allow compositions of probes and capture agents to flow in laminar fashion across the biological sample, ensuring that uneven staining (e.g., due to vortices, gradients, and other non-laminar flow phenomena) are controlled or even eliminated. Still further, the consistent chamber volumes and very small dead volumes (5 microliters or less) allow precise quantities of probe and capture agent compositions to be dispensed into the chamber, reducing waste and overflow. During sample processing, fluids can be made to move over the sample, or moved back-and-forth within the enclosed chamber, to agitate and enhance interaction between reagents in the fluids and components (e.g., targets) near the sample surface.

Another important advantage arises from the ability to disconnect the enclosed chamber (and the sample within) from different stations or locations in a processing system, and even from the system itself for storage. Because the sample is enclosed within the chamber, the substrate supporting the sample and the chamber can be moved among different locations and into storage, with the sample preserved within the chamber. Samples can subsequently be retrieved from storage after days, weeks, months, or even longer, and subjected to further processing and/or imaging steps. Further, components of the chamber can be removed, and the sample can be subjected to different types of analyses (e.g., DNA and/or RNA extraction and sequencing).

In an aspect, the disclosure features methods for analyzing a biological sample that include obtaining a biological sample mounted on a first substrate, affixing a second substrate to the first substrate to form an enclosed chamber on the first substrate with the biological sample positioned within an interior volume of the enclosed chamber, and performing multiple imaging cycles, where each imaging cycle includes: (a) binding a probe to the biological sample, (b) obtaining an image of the bound probe in the biological sample, and (c) removing at least a portion of the probe from the biological sample, where a thickness of the interior volume between the first and second substrates is 250 micrometers or less.

In another aspect, the disclosure features methods for analyzing a biological sample that include obtaining a biological sample mounted on a first substrate, affixing a second substrate to the first substrate to form an enclosed chamber on the first substrate with the biological sample positioned within an interior volume of the enclosed chamber, and performing multiple imaging cycles, wherein each imaging cycle includes: (a) binding a probe to the biological sample; (b) obtaining an image of the bound probe in the biological sample; and (c) removing at least a portion of the probe from the biological sample, where the first and second substrates are substantially transparent, and where an imaging window formed by the first and second substrates has a field of view of at least 500 mm$^2$.

In another aspect, the disclosure features methods for analyzing a biological sample that include obtaining a biological sample mounted on a first substrate, affixing a second substrate to the first substrate to form an enclosed chamber on the first substrate with the biological sample positioned within an interior volume of the enclosed chamber, and performing multiple imaging cycles, where each imaging cycle includes: (a) binding a probe to the biological sample, (b) obtaining an image of the bound probe in the biological sample, and (c) removing at least a portion of the probe from the biological sample, where the first substrate is formed of a glass and includes a first port that defines a first channel through the first substrate connected to the interior volume and a second port that defines a second channel through the first substrate connected to the interior volume, and where a closest distance between the first and second ports measured in a plane of the second substrate is 25 mm or more.

In another aspect, the disclosure features methods for analyzing a biological sample that include obtaining a biological sample mounted on a slide, contacting the slide with a gasket, the gasket having an aperture, where the sample is positioned within the aperture, and contacting the gasket with a window to enclose the sample within an interior volume bounded by the slide, gasket, and window, where the window defines a viewing area having a length of at least 25 mm and a width of at least 15 mm.

In another aspect, the disclosure features systems for analyzing a biological sample that include a labeling station having a fluidic apparatus, a translation apparatus, an imaging station having an image detector, and a controller connected to the fluidic apparatus, the translation apparatus, and the image detector, where the controller is configured so that during operation of the system, the controller: (a) obtains a first biological sample positioned on a first substrate and enclosed within a first chamber formed by the first substrate, a second substrate, and a gasket positioned between the first and second substrates, and obtains a second biological sample positioned on a third substrate and enclosed within a second chamber formed by the third substrate, a fourth substrate, and a gasket positioned between the third and fourth substrates; (b) positions the first biological sample at the labeling station using the translation apparatus and activates the fluidic apparatus to deliver a first labeling agent to the first biological sample within the first chamber; (c) positions the first biological sample at the imaging station using the translation apparatus and activates the image detector to obtain an image of the first labeling agent in the first biological sample; (d) with the first biological sample at the imaging station, positions the second biological sample at the labeling station using the translation apparatus and activates the fluidic apparatus to deliver a second labeling agent to the second biological sample within the second chamber; (e) removes the first biological sample from the imaging station; (f) positions the second biological sample at the imaging station and activates the image detector to obtain an image of the second labeling agent in the second biological sample; and (g) positions the first biological sample at the labeling station and activates the fluidic apparatus to remove at least a portion of the first labeling agent from the first biological sample, and to deliver a third labeling agent to the first biological sample.

Embodiments of any of the methods and systems disclosed herein can include any one or more of the following features.

The first substrate can be formed of a substantially transparent material, e.g., a glass or a plastic material. The first substrate can be a microscope slide. The second substrate can be a window.

The methods can include positioning a gasket between the first and second substrates. The gasket can be formed of an adhesive material.

The methods can include, prior to affixing the second substrate to the first substrate: incubating the biological sample in acetone; removing residual acetone from the biological sample; and affixing the second substrate to the first substrate following the removal of residual acetone. The methods can include, prior to incubating the biological sample in acetone: removing paraffin from the biological sample; and exposing the biological sample to an antigen retrieval agent.

The sample can be a fresh frozen sample. The sample can be a formalin-fixed, paraffin-embedded sample.

The methods can include, prior to performing the multiple imaging cycles, applying a stain to the biological sample.

The stain can include at least one member selected from the group consisting of a counterstain, a chromogenic stain, and an immunofluorescent stain. The stain can include at least one of DAPI and a Hoechst stain.

The second substrate can include a first port formed by a first aperture extending through a thickness of the second substrate and a second port formed by a second aperture extending through the thickness of the second substrate, where compositions are introduced into the interior volume through the first port. A minimum distance between the first and second ports measured in a plane of the second substrate can be 20 mm or more.

During each imaging cycle, the probe can be bound to the biological sample by introducing a composition that includes the probe through the first port, and removing components of the composition through the second port. The methods can include, prior to performing the multiple imaging cycles, binding a capture agent to the biological sample by introducing a composition that includes the capture agent through the first port.

The capture agent can include a binding agent that selectively binds to a sample component, and an oligonucleotide that is linked to the binding agent. The binding agent can include an antibody or an antibody fragment. The oligonucleotide can include at least 15 nucleic acids.

The composition can include multiple different types of capture agents, each of the different types of capture agents having a different type of binding agent that selectively binds to a different sample component, and an oligonucleotide that is specific to each different type of binding agent. The composition can include at least 5 different types of capture agents (e.g., at least 20 different types of capture agents). Each of the different types of capture agents can be bound to the biological sample by introducing the composition that includes each of the different types of capture agents at the same time into the interior volume of the enclosed chamber.

The probe can include an oligonucleotide that is at least partially complementary to the oligonucleotide of the capture agent, and a labeling agent linked to the oligonucleotide. The oligonucleotide of the probe can include at least 20 nucleic acids.

The labeling agent can include a fluorescent moiety.

Binding the probe to the biological sample can include binding one or more different types of probes to the biological sample, where each different type of probe includes a different type of oligonucleotide linked to a labeling agent that is specific to each different type of oligonucleotide.

The one or more different types of probes can include at least three different types of probes. The one or more different types of probes can be bound to the biological sample at the same time by introducing a composition that includes the one or more different types of probes into the interior volume of the enclosed chamber. The one or more different types of probes can bind to corresponding different types of capture agents in the biological sample. The one or more different types of probes can hybridize to the corresponding different types of capture agents in the biological sample.

The oligonucleotide of the probe can hybridize to the oligonucleotide of the capture agent, and removing at least a portion of the probe from the biological sample can include dehybridizing at least a portion of the probe from the capture agent. The methods can include dehybridizing the at least a portion of the probe from the capture agent by heating the biological sample and/or by introducing at least one dehybridizing agent into the interior volume of the enclosed chamber. The at least one dehybridizing agent can include a chaotropic agent.

The thickness of the interior volume can be 100 micrometers or less. The interior volume can be 0.20 cm$^3$ or less (e.g., 0.10 cm$^3$ or less).

The methods can include, prior to introducing a composition into the interior volume of the enclosed chamber, connecting a port coupler to at least one of the first and second ports. The port coupler can include a first member featuring at least one fluid channel that aligns with one of the first and second ports. Connecting the port coupler to the at least one of the first and second ports can include adhering the port coupler to a surface of the second substrate. The port coupler can include a second member, and connecting the port coupler to the at least one of the first and second ports can include connecting the first and second members of the port coupler to fix the port coupler in position relative to the second substrate. At least one of the first and second members can include at least one magnet, and the first and second members can be positioned such that the at least one magnet fixes the first and second members in position relative to the second substrate.

Embodiments of the methods and systems can also include any other features disclosed herein, and can include any combinations of features, including combinations of features that are individually described in connection with different embodiments, except as expressly stated otherwise.

Some embodiments described herein relate to a computer storage product with a nontransitory computer-readable medium (also can be referred to as a non-transitory processor-readable medium) having instructions or computer code thereon for performing various computer-implemented operations. The computer-readable medium (or processor-readable medium) is nontransitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™ Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

FIG. 5 is a schematic diagram of a system for analyzing a biological sample.

Like reference symbols in the various drawings indicate like elements.

DETAILED DESCRIPTION

Introduction

Figure 1A:
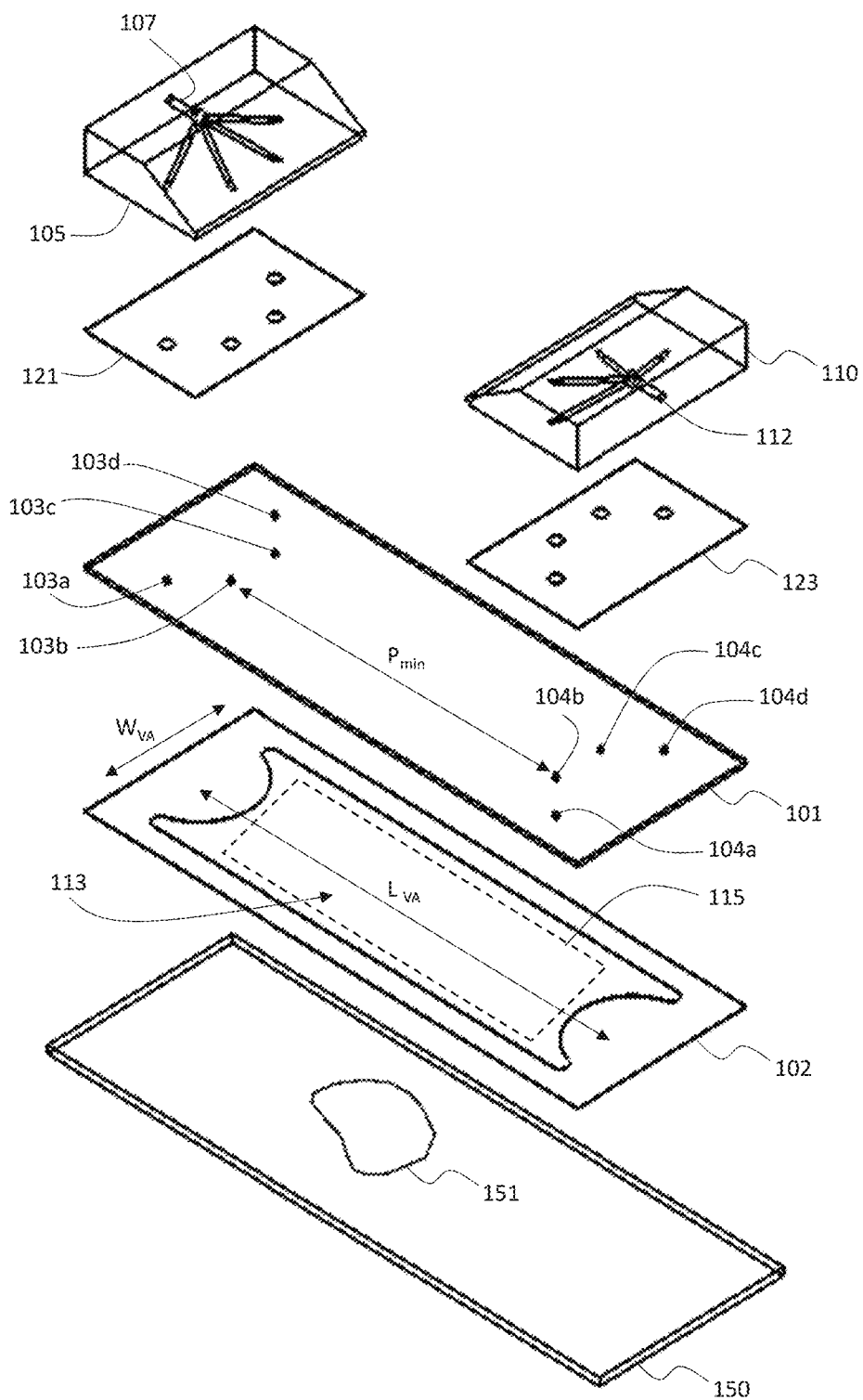
FIG. 1A is a schematic diagram showing an exploded view of a chamber formed on a substrate supporting a sample.

One technique for multiplex staining is a method called SIMPLE, described by Glass et al., *J. Histochem. Cytochem.* 57(10): 899-905 (2009). It involves immunostaining a sample using 3-amino-9-ethylcarbazole (AEC) as a detection system, attaching a coverslip, imaging with a brightfield microscope, removing it from the microscope, removing the coverslip, and destaining with ethanol to eliminate any visible AEC. This sequence is repeated for each target of interest in the sample.

A technique termed t-CyCIF is described by Lin et al. in *eLife* 2018, 7:e31657. It involves applying up to three antibodies to a sample, each of which is directly conjugated to a fluorescent label, applying a counterstain such as Hoechst 33342, applying a cover slip, imaging on a fluorescence microscope, removing the sample from the microscope, removing the coverslip, and bleaching the fluorophore with hydrogen peroxide and light to deactivate the dyes. This sequence is repeated for each group of targets in the sample, so an overall measurement can include many targets. The fluorescent dyes are directly conjugated to the antibodies, except in the final round, where secondary antibodies can be employed to obtain amplification.

These two techniques are not easily automated, take a long time to complete, and involve repeatedly applying and removing a cover slip, with associated manual handling and risk of damaging the sample. For at least these reasons, they are not easily deployed in settings where many samples are processed in a routine manner, such as in studies, clinical trials, or clinical care. However, they are flexible in the sense that the individual histology steps and imaging steps can be done using a wide range of apparatus depending on what is available and the measurement goals for the samples involved.

CODEX® reagents, methods, and systems for sample imaging are available from Akoya Biosciences (Menlo Park, CA), and permit multiplexed sample imaging. In particular, multiple oligo-conjugated antibodies are bound to multiple targets of interest, with a unique oligo sequence for each antibody. For each antibody, there is a label consisting of an oligo-conjugated fluorescent dye designed to hybridize with only this antibody. After incubation with all primary antibodies, a group of three labels is introduced, with distinct dyes, and they hybridize specifically to selected antibodies. The sample is imaged, where each dye corresponds to a given primary antibody. A de-hybridization is performed, and the labels are washed away. This cycle is repeated until all targets of interest have been imaged.

The CODEX® system includes staining and imaging apparatus. The sample is held in a glass-bottomed open well situated in the stage of an inverted microscope. Reagents are added to or removed from the chamber by automated fluidics. No sample handling is typically performed between cycles. Also, only one primary antibody incubation is typically used, so processing time is much less than for the SIMPLE or t-CyCIF methods. However, during a typical experiment, neither the imaging apparatus nor the staining apparatus can be used for other purposes. The use of an open chamber rather than a microscope slide enables automation, but a more standard sample format would be desirable. Various aspects of the methods, systems, and reagents associated with the CODEX® methodology are described in the following U.S. patents, the entire contents of each of which are incorporated herein by reference: U.S. Pat. Nos. 10,370,698; 9,909,167; 10,017,808; 10,000,796; and 10,006,082.

Overall, there is no technique at present for rapid sequentially stained IHC multiplexing in which the sample is not subjected to repeated coverslip attachment and removal, that is capable of processing samples that are provided on standard microscope slide format. Nor is there any existing technique for doing this in a fully automated way using a standard format. The methods and systems described herein image samples in workflows that involve multiple rounds of labeling, imaging, and label removal. The entire workflows can be performed in semi-automated or fully automated fashion. Further, the workflows can be performed with samples mounted on standard microscope slides. That is, the systems can perform sample handling, imaging, and labeling, such that labeling and de-labeling of multiple samples can be automated, and imaging can be performed on a wide range of manual or automated microscopes, with no sample reconfiguration or coverslip manipulation between steps or cycles.

Accordingly, sequentially stained multiplex IHC can be performed with very high throughput, where the apparatus for staining and imaging functions is run at high utilization, and the apparatus for one function is not idle while the other function is underway. The systems and methods can include or implement a modular sample enclosure for imaging and processing a sample on a microscope slide that incorporates a window through which the sample may be imaged and is set apart from the surface of the sample to create a microfluidic chamber. The chamber can include ports for introducing reagents to the sample and for removing them, can be easily handled, and can be connected or disconnected from fluidic sources.

In some embodiments, the sample is a tissue section or tissue microarray placed on a microscope slide, and the window is a thin piece of glass joined to the microscope slide by a perimeter seal that holds it a predetermined distance from the microscope slide. This distance is can be uniform within the region that forms the microfluidic chamber, and can be in the range of 40 to 250 microns. The systems and methods introduce and/or remove fluid reagents from the chamber formed by the window, slide, and seal. The fluid can be introduced to the microfluidic chamber via holes or apertures in the face of the window, and a manifold couples fluid from an entry port to the holes in the window. The manifolds are preferably arranged at opposite ends of the window, with the sample between them. The chamber design and flow rates produce laminar fluid flow over the sample.

The holes or apertures can be placed and sized to produce substantially similar flow rates over all regions of the sample. This promotes uniform staining over the sample, which is valuable in quantitative assays generally, especially in assays that incorporate amplification schemes such as hybridization or enzyme catalyzed deposition. Also, controlled flow is readily achieved to expose the sample to fresh reagent material at a predictable rate as it becomes depleted or exhausted. In some embodiments, the holes at one end of the window form an arc with equal spacing between holes, and all holes are equidistant from the input port of the associated manifold. This produces a uniform sheet flow over the sample. The same arrangement can be used at both manifolds.

In some embodiments, substrates hold multiple samples, each sample on its own microscope slide with a windowed microfluidic chamber enclosure, so large numbers of samples can be processed efficiently in groups.

Ports formed in the manifolds can couple fluid into or out of the chamber from/to a pipette tip, or tubing, or both. Tubing, if present, can incorporate quick-connect fixtures or other fittings for easily connecting the chamber to, or removing the chamber from connection with, automated fluidic assemblies and/or manual pipettes.

During sample processing within the enclosed chamber, reagents can remain in contact with the sample for prolonged times, permitting sample incubation. Samples undergoing incubation can be easily handled or moved without disturbing incubations that are underway.

The apparatus of the present invention can generally be used over a wide range of temperatures, typically from −4° C. to 45° C., and over any smaller range of temperatures within this range. The internal volume of the enclosed chamber can be relatively small, for example, approximately 40 microliters for a 4×2 cm window with a window-to-slide spacing of about 50 micrometers. Dead volumes within the enclosed chamber can be 5 microliters or less, reducing reagent volume and cost. More significantly, by realizing very small dead volumes, the residual amount of a given reagent remaining within the chamber following a removal step is very small, ensuring that contamination between steps is largely eliminated.

Typically, the enclosed chambers described herein are inexpensive to manufacture and simple to use, making them practical for use in a wide range of settings including academic research, translational studies, trials, and clinical care.

The methods described herein include multiplexed labeling and imaging of samples. Some methods pertain to multiplexed labeling and imaging of formalin-fixed paraffin embedded samples on microscope slides. Other methods pertain to labeling and imaging fresh-frozen samples.

To form a chamber that encloses a sample on a first substrate such as a microscope slide, a second substrate (e.g., a window such as a cover slip) is attached to the first substrate, spaced apart from the first substrate by a selected distance, with holes or apertures in the second substrate. Reagents are introduced, removed, and moved across the sample surface by directing the reagents to flow through these holes or apertures. These reagents are used to label components (e.g., molecular targets) in the sample, and the labels are imaged through the window using a microscope. One or more labels are removed, erased, or both, and then the cycle of labeling, imaging, and removal or erasure is repeated. In this way, a multiplexed image of a sample is obtained. This image can be analyzed to gain insight about the sample, or about the organism(s) from which it was extracted.

In some embodiments of this type, the sample is incubated with one or more primary antibodies before the fluidic chamber is formed by attaching the second substrate to the first substrate. In other embodiments, the primary antibody incubation is performed within the chamber after it is formed.

A variety of methods can be used to perform sequential staining and multiplexed imaging of biological samples. Without limitation, these include brightfield labeling with 3-amino-9-ethylcorbazole (AEC), where labels are erased using ethanol; direct-labeling of antibodies conjugated to fluorescent dyes, where labels are erased using hydrogen peroxide; indirect immuno-fluorescent labeling of primary antibodies, where fluorescent labels are erased by hydrogen peroxidase, or removed by stripping the primary antibody, secondary antibody, or both; labeling with oligo-conjugated fluorescent dyes that hybridize with counterpart oligo-sequences conjugated to antibodies, and labels are removed by dehybridization.

The methods can also include staining with histochemical dyes such as eosin, hematoxylin, 4′,6-diamidino-2-phenylindole (DAPI), periodic acid-Schiff stain (PAS), methylene blue, Hoechst stains (such as Hoechst 33342, Hoechst 34580, Hoechst 333258) and others, which are removed by ethanol or other solvents. These can provide information about the presence, location, and state of various cellular compartments, which is useful and complementary to molecular IHC information in many cases.

The methods can include fluorescent multiplexing with amplification as well. In one embodiments, primary antibodies are conjugated to unique oligo sequences; labeling uses an enzymatic catalyst such as horseradish peroxidase (HRP) conjugated to corresponding oligo sequences; one label species is introduced into the apparatus holding the sample and it hybridizes with its counterpart antibody; tyramide-signal amplification is used to deposit a fluorescent dye; and the label is dehybridized and washed away. This process can be repeated several times with different dyes having distinct spectra, and the sample is imaged. Optionally, the dyes can be inactivated afterward by use of hydrogen peroxide and light.

In some embodiments, rolling-circle amplification (RCA) can be used to amplify probes, or linear and/or branched oligo structures can be used to attach multiple dye molecules for each labeled antibody, in one or more cycles of labeling and imaging.

Further, any of the foregoing methods can be combined. For example, sample processing and analysis methods can include one or more rounds of IHC labeling, imaging, and label removal or erasure, together with one or more rounds of staining, imaging, and removal, with histochemical dyes.

The chamber enclosing the sample can remain in place across multiple imaging and labeling cycles. This is beneficial because the workflow is practical for processing large batches of samples or processing them in an automated fashion. Also, the sample is not vulnerable to damage from handling steps such as attaching or removing a window.

In some embodiments, information about the sample obtained from a given labeling and imaging cycle can be used to choose what targets are labeled and imaged in subsequent cycles. Thus, image acquisition can be tailored to the sample, as information about the sample emerges during the process. The modular nature of the sample handling makes it practical to sequester the samples, after the IHC cycles used to choose targets are complete, until a selection of sample components to be imaged in subsequent cycles has been made, whereupon sample processing resumes.

Sample Enclosures

As discussed above, the sample enclosures described herein are generally implemented by attaching one or more components to a substrate that supports a biological sample. A variety of different components can be used for this purpose. FIG. 1A is a schematic diagram showing an exploded view of components that are used to form one example of a sample enclosure. A first substrate 150 supports a biological sample 151 (e.g., a tissue section). To form an enclosure containing sample 151, a gasket 102 is attached to first substrate 150, and then a second substrate 101 is attached to gasket 102. Affixing second substrate 101 to first substrate 150 using gasket 102 creates a sealed chamber having an interior volume, the thickness of which is determined by the thickness of gasket 102. The field of view of the enclosed chamber is effectively defined by the open area 113 of gasket 102.

Second substrate 101 includes two or more ports to permit fluid flow into and out of the interior volume of the chamber. In general, each of the ports is formed as an aperture that extends through second substrate 101 and connects to the interior volume of the enclosed chamber. Second substrate 101 can have one or more inlet ports (e.g., two or more, three or more, four or more, five or more, or even more). Four inlet ports 103a-d are shown by way of example in FIG. 1A.

Second substrate 101 can also have one or more outlet ports (e.g., two or more, three or more, four or more, five or more, or even more). Four outlet ports 104a-d are shown by way of example in FIG. 1A.

An inlet manifold 105 can optionally be attached to second substrate 101 via an adhesive layer 121 with apertures that align with ports 103a-d. Fluid flowing into entrance port 107 in inlet manifold 105 is transported through interior manifold channels and into ports 103a-d, thereby introducing the fluid into the interior volume of the enclosed chamber. An outlet manifold 110 can optionally be attached to second substrate 101 via an adhesive layer 123 with apertures that align with ports 104a-d. Fluid flowing out of the interior volume of the enclosed chamber is transported through outlet ports 104a-d and into manifold 110, where it is discharged from exit port 112.

As discussed above, the foregoing components, once assembled, form an enclosed chamber around sample 151, which is positioned within the interior volume of the chamber. Reagents, compositions, and other fluids (and fluid-supported compounds) can be introduced into the interior volume to contact, react with, bind to, and otherwise interact with sample 151. Fluids, components of compositions, and reagents can also be extracted from the interior volume, for example by connecting a pump, a vacuum source, or a similar component to one or more outlet ports of the sample enclosure.

In FIG. 1A, the thickness of the interior volume of the enclosed chamber—measured in a direction perpendicular to the sample-supporting surface of substrate 150—is determined by the thickness of gasket 102. Alternatively, in certain embodiments, the thickness of the interior volume of the enclosed chamber is determined, at least in part, by other components of the chamber. In some embodiments, the thickness of the interior volume is 250 micrometers or less (e.g., 200 micrometers or less, 150 micrometers or less, 125 micrometers or less, 100 micrometers or less, 75 micrometers or less, 50 micrometers or less, 40 micrometers or less, 30 micrometers or less).

In particular, it has been observed that within a range of thicknesses of between 30 micrometers and 250 micrometers, laminar fluid flow is promoted, ensuring intimate contact between fresh reagents and the sample, and therefore reducing sample processing times relative to processing with more turbulent fluid flows. Moreover, because the interior volume of the enclosed chamber is relatively small in comparison to reagent volumes used in bench processes and autostainers, reagent consumption is reduced relative to these techniques. Accordingly, sample processing can occur faster and/or more economically when compared with these alternatives.

In some embodiments, the interior volume of the enclosed chamber is 0.40 cm$^3$ or less (e.g., 0.35 cm$^3$ or less, 0.30 cm$^3$ or less, 0.25 cm$^3$ or less, 0.20 cm$^3$ or less, 0.15 cm$^3$ or less, 0.10 cm$^3$ or less, 0.08 cm$^3$ or less, 0.07 cm$^3$ or less, 0.06 cm$^3$ or less, 0.05 cm$^3$ or less, 0.04 cm$^3$ or less, 0.03 cm$^3$ or less, 0.02 cm$^3$ or less, 0.01 cm$^3$ or less).

Either or both of substrates 150 and 101 can be substantially transparent in FIG. 1A. As used herein, "substantially transparent" means that less than 25% of incident radiation at any wavelength from 450 nm to 650 nm is absorbed or reflected by the substrate. With substrates 150 and 101 substantially transparent and manifolds 105 and 110 located at the edges of substrate 101, the field of view of the enclosed chamber is defined by the open area 113 of gasket 102 in FIG. 1A. Alternatively, in some embodiments, other components used to form the enclosed chamber (such as one or more manifolds, substrates 101 and/or 150, and optional spatial filtering layers, define the field of view of the enclosed chamber.

As used herein, the "field of view" of the enclosed chamber is the area of the largest rectangular or square substantially transparent window through which a sample on substrate 150 can be imaged. The field of view is represented by the dotted rectangle 115 in FIG. 1A. It should be noted that the field of view can be larger than a cross-sectional area of a particular sample. In some embodiments, the field of view is at least 300 mm$^2$ (e.g., at least 350 mm$^2$, at least 400 mm$^2$, at least 450 mm$^2$, at least 500 mm$^2$, at least 550 mm$^2$, at least 600 mm$^2$, at least 650 mm$^2$, at least 700 mm$^2$, at least 750 mm$^2$).

As used herein, the "viewing area" of the enclosed chamber is the area of the substantially transparent window through which a sample on substrate 150 can be imaged. The viewing area can be equal to or larger than the field of view. The length of the viewing area is the maximum dimension of the viewing area in a direction parallel to one of the sides of substrate 150, and the width of the viewing area is the maximum dimension of the viewing area in a direction orthogonal to the length, with the width smaller than the length. The respective length ($L_{VA}$) and width ($W_{VA}$) of the viewing area are shown in FIG. 1A.

In some embodiments, the length of the viewing area is 20 mm or more (e.g., 25 mm or more, 30 mm or more, 35 mm or more, 40 mm or more, 45 mm or more, 50 mm or more, 55 mm or more, 60 mm or more, 65 mm or more, 70 mm or more). In certain embodiments, the width of the viewing area is 10 mm or more (e.g., 15 mm or more, 20 mm or more, 25 mm or more, 30 mm or more).

The substrates, gasket, ports, and manifolds, can be dimensioned and located to produce laminar reagent flow over sample 151 on substrate 150. Sample 151 can therefore be labeled, imaged, and de-labeled within the interior volume of the enclosed chamber. To ensure relatively uniform staining or labeling, the flow of reagents to sample 151 can be relatively similar at all locations on the sample surface. This is particularly important during processing that is strongly dependent on reagent concentration, or time, or in which the reagent becomes depleted by its interaction with the sample, or which do not normally run to saturation but instead produce a result that is dependent on kinetics. One example of such processing is IHC label amplification steps.

Approximate uniformity of reagent or composition flow across sample 151 can be achieved in several ways. For example, in certain embodiments as shown in FIG. 1A, manifold 105 includes multiple flow channels coupled to multiple input ports 103a-d, and the impedance to fluid flow along the fluid flow paths defined by the flow channels and input ports are substantially the same. Input ports 103a-d are arranged along an arc within the enclosed chamber to assist in matching the impedances, and substantially equal flow volumes are delivered through the ports. Because of the chamber and port locations and dimensions, flow is laminar at flow rates used for sample processing. Fluid introduced as individual streams at the input ports forms a continuous sheet of flow within a few millimeters after entering the chamber. As a result, the sample experiences uniform processing with minimal reagent gradients.

Sample processing, in some embodiments, involves flowing a series of reagents over the sample in turn. As a new reagent is introduced to the input port(s), the fluid enters the chamber in a front whose shape is determined by the arrangement of ports. Here the term front is used to indicate the delineation where the chamber contents change from being one reagent to the next.

In this example, the front forms an arc due to the arrangement of input ports. As each new reagent is introduced, this front moves along the slide, traveling from one manifold to the other. Typically, at least enough of the new reagent is introduced to ensure that the front has traveled entirely past the sample region. Because laminar flow occurs within the enclosed chamber, evacuation of the previous reagent is rapid, and the number of fluid exchanges required to produce a complete overturning of reagents is low compared with other slide-based sample processing approaches. In some cases, all that is required is to advance the front past the sample region. In other cases, a several-fold larger amount of new reagent is introduced, so not even a trace amount of the earlier one remains in the sample region.

In general, second substrate 101 can include one or more inlet ports 103 (e.g., two or more, three or more, four or more, five or more, or even more). Further, second substrate 101 can include one or more outlet ports 104 (e.g., two or more, three or more, four or more, five or more, or even more). In general, inlet ports 103 are positioned closer to a first side of second substrate 101 and outlet ports 104 are positioned closer to a second side of second substrate 101 opposite to the first side. Typically, inlet and outlet ports are positioned on opposite sides of second substrate 101 so that fluids introduced through inlet port(s) 103 and removed through outlet port(s) 104 will flow over the surface of sample 151 during transport between the ports.

In some embodiments, as shown in FIG. 1A, a minimum or closest distance $p_{min}$ between any of the inlet ports 103 and any of the outlet ports 104, measured in a plane of the second substrate, is 20 mm or more (e.g., 25 mm or more, 30 mm or more, 35 mm or more, 40 mm or more, 45 mm or more, 50 mm or more, 55 mm or more, 60 mm or more, 65 mm or more, or even more). Where second substrate 101 includes only two ports, the minimum distance is the closest distance between the two ports in the plane of second substrate 101.

The first substrate 150 can be formed from a variety of materials including, but not limited to, various glasses and/or plastic materials. For example, first substrate 150 can be a microscope slide. Second substrate 101 can also be formed from a variety of materials including, but not limited to, various glasses and/or plastic materials. As an example, second substrate 101 can be a window such as, but not limited to, a cover slip or another type of planar member. In some embodiments, second substrate 101 is implemented as a piece of 0.5 mm thick Corning Eagle XG glass (Corning, NY), 24×55 mm in extent.

First substrate 150 can generally have a thickness of 1.1 mm or less (e.g., 1.0 mm or less, 0.9 mm or less, 0.8 mm or less, 0.7 mm or less, 0.6 mm or less, 0.5 mm or less, 0.4 mm or less, 0.3 mm or less, 0.2 mm or less, 0.1 mm or less). Second substrate 101 can generally have a thickness of 1.1 mm or less (e.g., 1.0 mm or less, 0.9 mm or less, 0.8 mm or less, 0.7 mm or, less, 0.6 mm or less, 0.5 mm or less, 0.4 mm or less, 0.3 mm or less, 0.25 mm or less, 0.2 mm or less, 0.1 mm or less).

In general, manifolds 105 and 110 can be formed from a variety of materials, including plastics, rubber-based materials, and metals. In some embodiments, for example, manifolds 105 and/or 110 are formed of polyether ether ketone (PEEK), solid-printed to provide the ports and internal pipes connecting them.

Gasket 102 is generally implemented as a pressure-sensitive adhesive chosen for good adhesion and chemical compatibility for the reagents, wash agents, and other fluids used in processing. In embodiments where the gasket thickness determines the thickness of the chamber's internal volume, selection of the gasket provides a way to select the chamber thickness to a desired value. In some embodiments, for example, gasket 102 can be formed from an acrylic material, such as 3M Adhesive transfer tape 966 (3M, St. Paul, MN) though other materials may be preferred in other situations, according to the thickness desired and the chemical properties of the reagents used in the processing.

Adhesive layers 121 and/or 123 can generally correspond to pressure sensitive adhesives as described above. Alternatively, epoxies or other adhesives can be used, such as Master Bond EP21LV (Hackensack, NJ). In general, the adhesive layers provide a liquid-tight seal between the manifolds and the second substrate without interfering with fluid flow. Criteria for selection include chemical compatibility with the reagents to be used in the sample processing, and its adhesion to glass and the surface of the manifold involved.

Other techniques can also be used to produce uniform flow with different geometries. For example, the manifolds can have channels of different lengths, with diameters selected to achieve approximately equal flow rates/volumes at inlet ports.

The terms input ports and output ports are used above for clarity in the discussion, and fluid flow may be entirely or primarily in one direction. However, the enclosed chamber can be operated with fluid flow in either direction if that is beneficial for a particular sample processing operation. For example, flow can be cycled in either direction to achieve an effect like that achieved by rocking agitation during bench processing, namely, to promote interaction between the sample and the reagent. Also, such action reduces the degree to which localized sample reactions deplete the reagents near them, by cycling what reagent volume interacts with what sample regions.

In FIG. 1A, manifolds 105 and 110 provide a single aperture or port for fluid input and output. This can be coupled to tubing by pressing a short length of #19-gauge stainless steel hypodermic stock into the port and attaching tubing to the protruding portion of that stock using friction fit to a properly-sized piece of tubing. That tubing can include quick-connect fittings at the other end, if desired.

Alternative connection schemes are possible, in which manifolds 105 and/or 110 incorporate an elastomeric seal such as an o-ring, so that a pipette can be brought into direct contact with input and/or output ports 107 and/or 112. This can be advantageous in circumstances where reagents are limited or costly, since it keeps dead volumes to a minimum. Since the volume needed to fill the chamber can be quite small, the overall arrangement is very efficient in terms of reagent usage. In some embodiments, for example, the overall dead volume within the enclosed chamber is 5 microliters or less (e.g., 4 microliters or less, 3 microliters or less, 2 microliters or less, 1 microliter or less).

A variety of different connections between the manifolds and external fluidic apparatus is possible, so that the same manifold could at various times be connected to a pipette, or a pressure-fitted piece of tubing. In this way, the same enclosed chamber can be readily connected to manual fluidic items such as pipettes, or to automated fluidic apparatus via tubing or other arrangements.

Figure 1B:
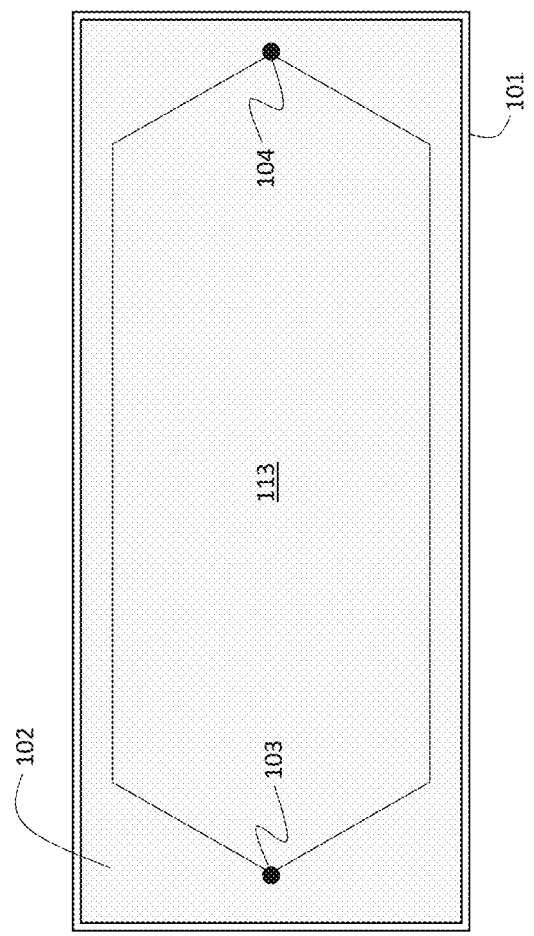
FIG. 1B is a schematic diagram showing an example of a gasket used to form a chamber.

One example of an enclosed chamber is shown in FIG. 1A. However, the enclosed chambers described herein can be implemented in a variety of ways. FIG. 1B shows a top view of another example of an enclosed chamber formed by a first substrate 150, a gasket 102, and a second substrate 101 (first substrate 150 is not shown in FIG. 1B for clarity). As shown in FIG. 1B, the chamber includes a single input port 103 and a single output port 104, each formed as apertures in second substrate 101 that extend through the thickness of the substrate. The open area 113 of gasket 102 is shaped as an irregular hexagon (i.e., a hexagonal shape with non-uniform side lengths). Ports 103 and 104 are positioned along a central axis of the gasket, at opposite vertices of the hexagonal opening. Gasket 102 in FIG. 1B can have any one or more of the attributes discussed above in connection with gasket 102 of FIG. 1A.

Figure 1C:
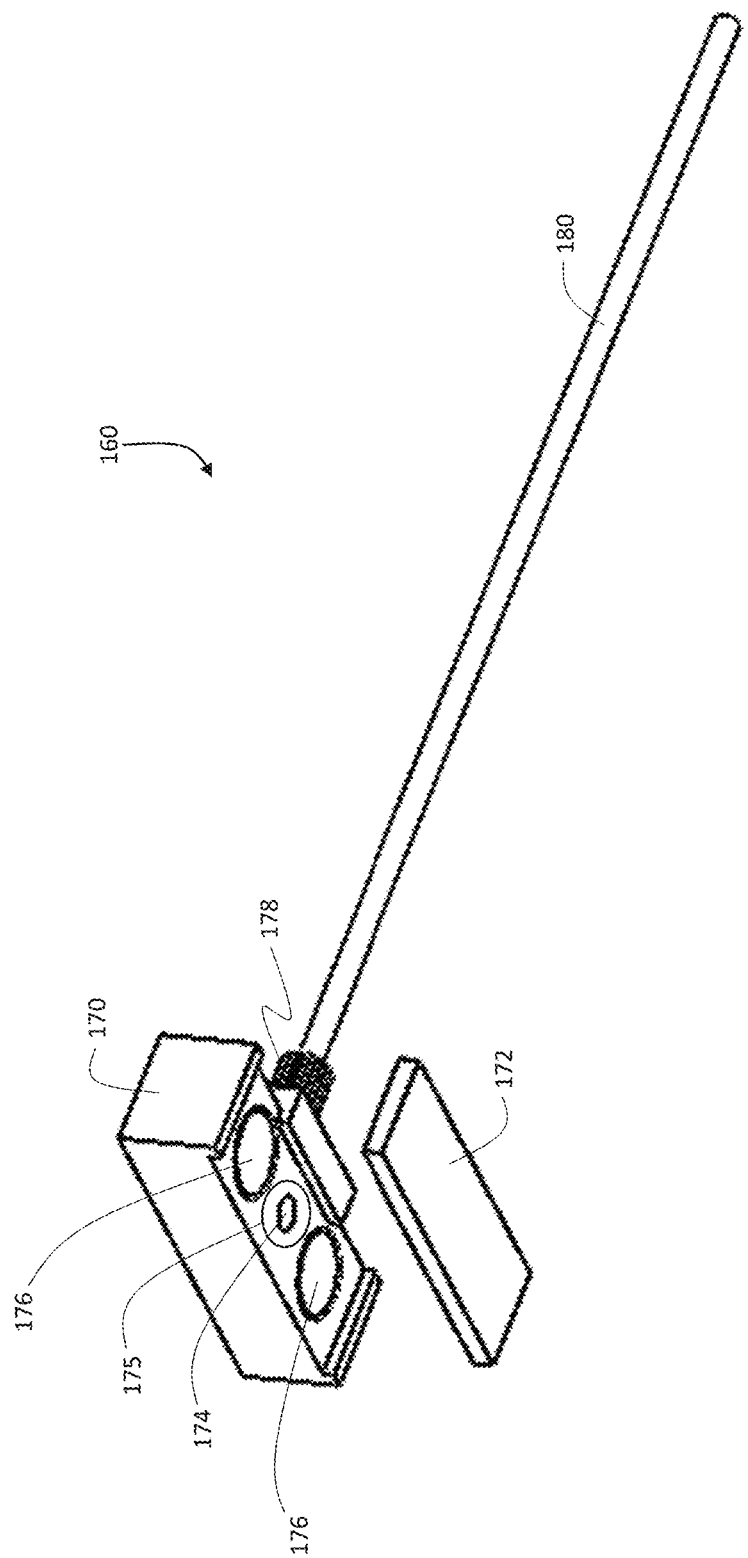
FIG. 1C is a schematic diagram showing an example of a port coupler.

Manifolds 105 and 107 can also be referred to as port couplers, particularly where the enclosed chamber includes a single input port and/or single output port. In addition to manifolds 105 and 107, other implementations of port couplers can also be used. For example, FIG. 1C shows a schematic diagram of another example of a port coupler 160. Port coupler 160 includes a first member 170 and a second member 172. Magnets 176 are embedded within the body of first member 170 (optionally, magnets can be embedded within the body of second member 172 as an alternative to, or in addition to, first member 170). Member 172 is formed of a magnet material such as stainless steel. First member 170 includes an aperture 174 that connects to port 103 or port 104 (FIG. 1B). Within first member 170, aperture 174 is connected via an internal channel to port 178, which in turn is connected to a fluid conduit 180.

To engage port coupler 160 with second substrate 101, the first member 170 is positioned on top of second substrate 101, with aperture 174 in alignment with port 103 or 104. The second member 172 is positioned opposite first member 170 on the underside of first substrate 150. Magnetic force between magnets 176 and second member 172 ensures that port coupler 160 remains fixed in position.

A variety of other locking mechanisms can also be used to secure members 170 and 172 to second substrate 101. For example, in some embodiments, mechanisms such as clasps, latches, pins, tabs, and keys can be used to lock members 170 and 172 in position with respect to one another, and to second substrate 101. As another alternative, members 170 and/or 172 can be affixed relative to second substrate 101 using adhesives, such as any of the adhesives described previously. When adhesives are used, second member 172 may be eliminated if desired.

In some embodiments, a sealing member or layer is positioned between port coupler 160 and second substrate 101 to ensure that a fluid-tight seal is formed between aperture 174 and port 103 or 104. In some embodiments, as shown in FIG. 1C, an elastomeric member such as a sealing ring 175 is positioned on first member 170 or second substrate 101. The elastomeric member 175 is compressed between first member 170 and second substrate 101, forming the seal. Alternatively, in certain embodiments, an elastomeric sheet (similar to layer 121 in FIG. 1A) is positioned on first member 170 or second substrate 101, and is compressed between first member 170 and second substrate 101 to form the seal.

Sample Preparation Methods

As discussed above, the enclosed chambers described herein can be formed on substrates that support a variety of samples. Examples of such samples include, but are not limited to, fresh tissues such as biopsy sections, fresh-frozen (FF) tissue sections, and formalin-fixed, paraffin-embedded (FFPE) tissue sections. The methods described here are generally used to perform one or more cycles of immuno-histochemical staining and imaging of biological samples enclosed within a chamber formed as described above.

Figure 2:
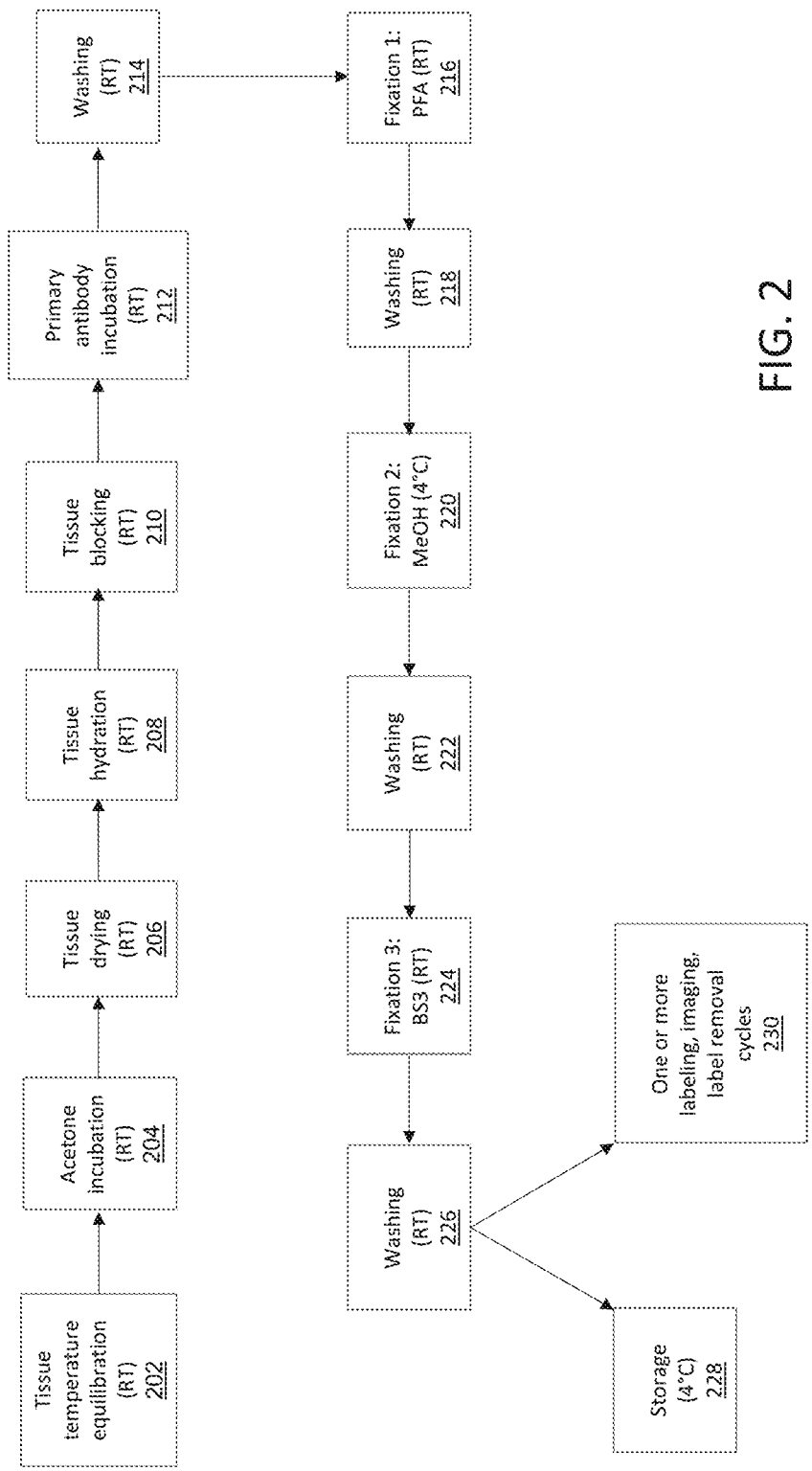
FIG. 2 is a flow chart showing example steps for labeling and imaging a fresh-frozen tissue sample.

FIG. 2 is a flow chart showing a series of example steps for labeling and imaging a FF tissue section. In a first step 202, the FF tissue section is equilibrated to room temperature, e.g., by actively heating the tissue section, or by passively allowing the tissue section to warm up under ambient conditions. Next, in step 204, the tissue section is fixed by incubating the tissue section in an acetone bath at room temperature for a period of, for example, 10 minutes. Then, in step 206, the tissue section is dried by allowing residual acetone in the tissue section to evaporate, either passively or with heating.

Next, in step 208, the tissue is hydrated in solution (e.g., in a solution such as potassium-buffered sodium (PBS) for a few minutes), and then in step 210, a tissue blocking step is performed. Next, in step 212, the tissue section is incubated with one or more capture agents, each of which includes a primary antibody that specifically binds to a component (e.g., a target) in the sample. Following primary antibody incubation, the tissue section is washed in step 214 and undergoes a first fixation in an aqueous paraformaldehyde (PFA) solution in step 216.

Next, the tissue section is washed in step 218 and undergoes a second methanol fixation step 220. After washing again at step 222, the tissue section undergoes a bovine serum albumin (BSA) fixation step 224. Finally, the sample is washed again at step 226, and either delivered to storage in step 228, or subjected to one or more labeling and imaging cycles 230.

Within the example steps shown in FIG. 2, the enclosed chamber can be formed as described above at any point in the workflow after step 206. That is, at any time after residual acetone has been removed from the tissue section in step 206, the enclosed chamber can be formed, and subsequent sample processing steps can be carried out by introducing fluids, reagents, and compositions through one or more input ports 103, and removing fluids, reagents, and compositions (and components thereof) through one or more output ports 104.

Figure 3:
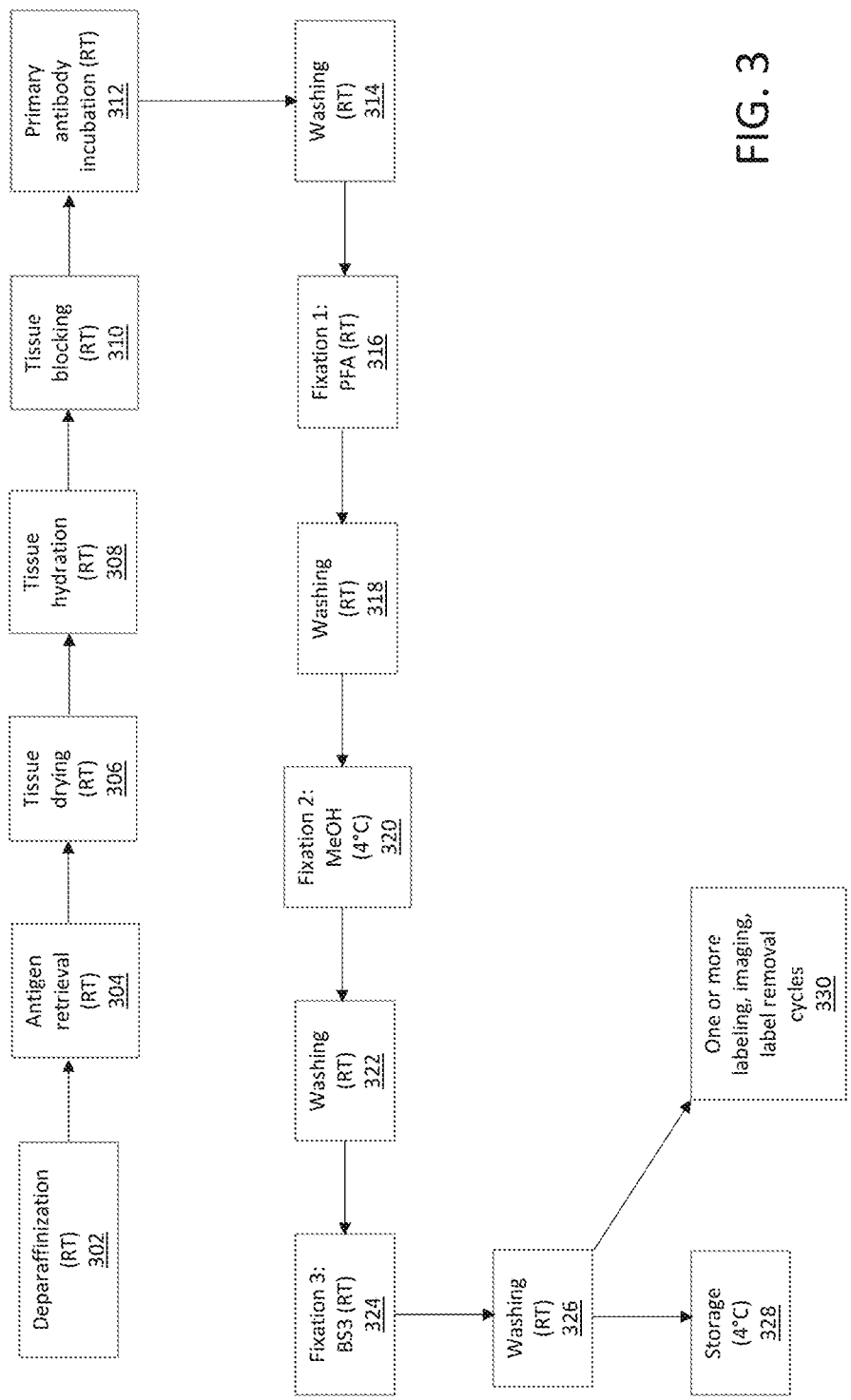
FIG. 3 is a flow chart showing example steps for labeling and imaging a formalin-fixed, paraffin-embedded tissue sample.

FIG. 3 is a flow chart showing a series of example steps for labeling and imaging a FFPE tissue section. In a first step 302, the tissue section is deparaffinized using any of various well-known deparaffinization protocols, e.g., using successive xylene and ethanol washes.

Next, in step 304, antigen retrieval (AR) is performed. Many techniques exist for AR, and selection of an appropriate technique depends on factors such as the tissue type, fixation conditions, and the target epitopes which are to be detected with the IHC labeling. For example, conventional techniques for AR which can be used include heat-induced epitope retrieval (HIER) and proteolysis-induced epitope retrieval (PIER). These techniques can be performed with sample 151 on first substrate 150 (e.g., on a microscope slide) as is conventional practice. Following AR, the tissue section is washed (e.g., in a PBS solution) to remove residual AR reagents, and dried in step 306.

The subsequent steps 308, 310, 312, 314, 316, 318, 320, 322, 324, 326, 328, and 330 are similar to corresponding steps 208-230 discussed above, and so the discussion of these steps is not repeated.

Within the example steps shown in FIG. 3, the enclosed chamber can be formed as described above at any point in the workflow after step 302. That is, at any time after deparaffinization, the tissue section can be rinsed in ethanol, acetone, toluene, or another non-aqueous solvent, the residual solvent is removed from the sample by drying, and the enclosed chamber can be formed, and subsequent sample processing steps can be carried out by introducing fluids, reagents, and compositions through one or more input ports 103, and removing fluids, reagents, and compositions (and components thereof) through one or more output ports 104.

Sample Analysis Workflows

The preparative steps described above can be used as precursors to a variety of different labeling and imaging workflows corresponding to steps 230 and 330 in FIGS. 2 and 3. It should be noted that in steps 228 and 328, prepared samples can be delivered to a storage facility within the enclosed chambers formed as described above. For example, samples can be stored at low temperature (e.g., approximately 4° C.) and retrieved from storage and warmed to room temperature for labeling and imaging purposes at a later date and time (e.g., one or more hours, days, weeks, months, or even longer, after preparation). In some embodiments, prepared samples can undergo one or more labeling and imaging cycles, and then can be sent to (or returned to) storage at a storage location or facility. The same samples, still within the enclosed chambers, can subsequently be retrieved for additional labeling and imaging cycles. Samples can be sent to and retrieved from storage multiple times, and some or all of the labeling and imaging steps can be repeated after intervals of sample storage.

In addition, following the completion of the labeling and imaging cycles (and, in some embodiments, after retrieving samples from storage once again), chamber enclosing the sample can be removed (e.g., by mechanically peeling away the second substrate 101, and sample 151 can be analyzed further using additional analytical techniques. For example, sample 151 can be subjected to genetic analysis in which sample cells are lysed, DNA and/or RNA is collected, and the collected nucleic acids are sequenced, e.g., using any of a variety of different next-generation sequencing (NGS) techniques.

The ability to review images obtained after one or more cycles of labeling and imaging, and then repeat one or more labeling and imaging steps (e.g., to verify imaging parameter such as exposure times, and/or to detect weakly expressed sample components) offers significant advantages relative to conventional IHC methods in which samples are generally not re-labeled and imaged, particularly after storage for a period of time. Further, intermittent storage of samples followed by retrieval and resumption of labeling and imaging cycles permits users to schedule analyses according to laboratory schedules and priorities.

A variety different labeling and imaging workflows can be used in steps 230 and 330. Each of the workflows can involve a single labeling and imaging step, or multiple labeling and imaging steps (e.g., multiple labeling and imaging cycles). Examples of these different types of workflows are described below.

Nonsequential IHC

In some embodiments, a single round of labeling and imaging of a biological sample in an enclosed chamber is performed. Labels applied to the sample can be removed, but can also remain in the sample after imaging. To label the sample, compositions (e.g., fluid-based compositions) that include one or more labels or stains are delivered into the enclosed chamber via one or more ports 103, and the labels or stains interact with the sample relatively quickly following introduction in comparison with conventional methods for sample processing. The compositions can be delivered by an automated fluidic assembly, or introduced manually by a technician.

In some embodiments, compositions delivered into the enclosed chamber include a single type of label or stain that binds to a specific type of component (e.g., target) in the sample, such as a particular antigen or expressed protein marker. In certain embodiments, compositions delivered into the enclosed chamber include multiple different types of labels or stains, each of which specifically binds to a different type of component (e.g., target) in the sample.

For example, in some embodiments, each of the different types of labels can include a primary antibody or antibody fragment linked to a fluorescent labeling agent. The primary antibody or antibody fragment binds to a specific component (e.g., target antigen or protein) in the sample. By exposing the labeling agent to incident light and obtaining an image of fluorescence emission from the labeling agent, the spatial distribution and quantitative amount of the corresponding component in the sample can be determined.

In some embodiments, tyramide signal amplification (TSA) can be used to label a sample for imaging. For a component of interest in the sample, a first composition is delivered to the sample containing a primary antibody or antibody fragment that specifically binds to the component. Then, a second composition that includes a secondary antibody that specifically binds to the primary antibody is introduced. Linked to the secondary antibody is an enzymatic catalyst (e.g., horseradish peroxidase (HRP)). Next, a third composition that includes tyramide labeled with a labeling agent is introduced, and the enzymatic catalyst catalyzes the conversion of tyramide into tyramide radical, which then binds to tyrosine residues proximal to the location of the primary antibody. In this manner, significant amplification of the fluorescence signal corresponding to the component can be achieved. Aspects of TSA are described for example in Toth et al., *J. Histochem. Cytochem.* 55(6); 545-554 (2007), the entire contents of which are incorporated herein by reference.

In some embodiments, instead of a direct conjugation between the secondary antibody and the enzymatic catalyst, the secondary antibody can be biotinylated and the enzymatic catalyst (e.g., HRP) can be conjugated to streptavidin. The secondary antibody is delivered first to the sample, followed by the enzymatic catalyst to bind the catalyst selectively to the secondary antibody, after which TSA proceeds as discussed above.

In certain embodiments, one or more stains can be applied to the sample. Stains can be applied before, during, or after one or more cycles of labeling and imaging, following standard staining protocols. Stains can be applied to samples by delivering staining solutions into the enclosed chamber, or alternatively, prior to formation of the enclosed chamber. A variety of different stains can be used including, but not limited to, DAPI, any of the Hoechst stains, hematoxylin, and eosin, and including combinations of multiple stains.

In all of the foregoing workflows, images of labels and stains in samples are obtained using an imaging detector such as a CCD camera or CMOS detector. Incident radiation from a source is directed to stained/labeled sample, and light emitted from the sample is detected (e.g., imaged) by the detector. In some embodiments, where the sample contains an absorptive (e.g., chromogenic) stain such as a counterstain, the light emitted from the sample generally corresponds to incident light transmitted from or reflected by the sample. Where the sample contains a fluorescent stain (e.g., an immunofluorescent stain), the light emitted from the sample generally corresponds to fluorescence emission from the stain in response to the incident radiation.

Where the sample contains a fluorescent label (e.g., a fluorescent moiety that is specifically bound to, or associated with, a particular component (target) in the sample), incident radiation causes the label to emit fluorescence which is imaged by the detector. The quantity and spatial distribution of the fluorescence emission can be used to quantitatively determine, at each location in the sample, a relative amount of the component (target).

Examples of chromogenic stains that can be used include, but are not limited to, xanthene-based dyes, such as a fluorescein dye and/or a rhodamine dye. Examples of suitable fluorescein and rhodamine dyes include, but are not limited to, fluorescein isothiocyanate (FITC), 6-carboxyfluorescein (commonly known by the abbreviations FAM and F), 6-carboxy-2',4',7',4,7-hexachlorofluorescein (HEX), 6-carboxy-4', 5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110. Chromogenic statins can also include a cyanine-based dye. Suitable examples of such dyes include, but are not limited to, the dyes Cy3, Cy5 and Cy7. The chromogenic stain can also be a coumarin dye (e.g., umbelliferone), a benzimide dye (e.g., any of the Hoechst dyes such as Hoechst 33258), a phenanthridine dye (e.g., Texas Red), an ethidium dyes, an acridine dyes, a carbazole dye, a phenoxazine dye, a porphyrin dye, a polymethine dye (e.g., any of the BODIPY dyes), and a quinoline dye.

Examples of immunofluorescent stains that can be used include, but are not limited to, pyrenes, coumarins, diethylaminocoumarins, FAM, fluorescein chlorotriazinyl, fluorescein, R1 10, JOE, R6G, tetramethylrhodamine, TAMRA, lissamine, napthofluorescein, Texas Red, Cy3, and Cy5.

Sequentially Stained Multiplex IHC

In addition to a single round of simple or multiplexed IHC labeling, multiplexed IHC labeling and imaging via sequential labeling and imaging cycles can be implemented. In the workflow depicted in FIG. 2, an oligo-labeled multiplex analysis is performed. In this type of analysis, there is a single incubation with primary antibodies followed by rounds of oligo-mediated labeling via hybridization, imaging of the labels, de-hybridization, and removal of the labels via wash steps.

The sample can be subjected to acetone fixation and evaporation. Subsequently, the enclosed chamber is formed with the sample within the interior volume of the chamber. Primary incubation steps can be performed by direct pipette injection into the enclosed chamber. Fixation and the cyclical labeling, imaging, and label removal can be performed by an automated fluidic system, such as that used in the Akoya CODEX® platform (Akoya Biosciences, Menlo Park, CA), connected to the input and output ports 103 and 104 of the chamber.

After each round of labeling, the sample can be imaged using a microscope with an automated stage. For example, the microscope can use a Nikon CFI S Plan Fluor ELWD 20XC, with NA of 0.45. Its focus collar can be set to compensate for the thickness of the window and fluid layers that lie between the sample and the objective. This compensation can be performed by adjustment prior to the onset of staining, or by whatever method is preferred, such that the objective is configured for proper imaging with the actual materials and thicknesses that are present during the serial imaging steps. Other objectives can be used instead, including but not limited to the Nikon CFI S Plan Fluor LWD 20XC, with NA of 0.70.

In general, the enclosed chambers described herein can be used with any workflow that permits cyclical labeling, imaging, and label removal from a sample. Methods that involve these steps after a single primary incubation are particularly advantageous due to reduced analysis time arising from introduction of all primary antibodies into the sample in a single incubation step. However, methods involving multiple incubation steps with primary antibodies (e.g., interleaved between labeling and imaging cycles) can also be implemented, as can methods that do not involve separate primary antibody incubation following by additional labeling prior to imaging.

In certain embodiments, following primary antibody incubation, one or more labeling and imaging cycles can be performed in which amplification of the label occurs when the sample is labeled. A variety of different methods can be used for amplification, including oligo-mediated labeling that incorporates rolling circle amplification (RCA), branch- or ligation-amplification (BLA), oligo-linked enzymatic amplification such as tyramide-signal amplification (TSA) using oligo-conjugated HRP, and combinations of these techniques.

One or more labeling and imaging cycles can also be performed in which amplification of the label does not occur. Further, in some embodiments, a first cycle of labeling, imaging, and label removal is performed using one type of labeling such as non-amplified oligo-labeling, and a further cycle is performed (immediately afterward, or after additional cycles) based on amplified labeling such as RCA, BLA, or TSA. In other embodiments, the order of the cycles is reversed.

In certain embodiments in which one or more labeling and imaging cycles are performed, label removal may be omitted in any cycle, such as in the final cycle. This saves time and effort and leaves the sample in a state where it may be imaged again in the future with the last-applied labels present. It should be noted that TSA reactions deposit compounds in the sample that are less easily removed from the sample than some of the other workflows described herein, and the compounds can interfere with subsequent labeling and/or imaging. Accordingly, in some embodiments, it can be advantageous to use TSA-based labeling reactions after other cycles have been completed.

In some embodiments, one or more samples, each enclosed in a corresponding chamber, is processed by a system with an automated labeling station with a fluidic assembly and an automated imaging station with an image detector. The system can optionally perform primary incubation and sample fixation steps, or these steps can be performed manually by a technician. The system performs one or more imaging cycles (e.g., labeling, imaging, and label removal) in fully automated fashion, with no user intervention. For analysis of multiple samples, fluidic and imaging operations can be interleaved among the samples for improved efficiency. For example, when four samples are analyzed, the first sample can undergo automated incubation with primary antibodies, the system can deliver a probe as part of a labeling and imaging cycle to the second sample, the system can obtain an image of one or more labeling agents introduced into the third sample as part of a labeling and imaging cycle, and the system can deliver a label removal agent as part of a labeling and imaging cycle to the fourth sample.

IHC and Histological Staining

In some embodiments, one or more cycles of IHC (e.g., labeling and imaging cycles) can be performed, followed by histological staining of that sample. Alternatively, histological staining can be performed prior to performing one or more cycles of IHC (e.g., labeling and imaging cycles) on the sample.

There is a wide range of histology dyes that can be used in such workflows. For example, by combining histological staining and one or more labeling and imaging cycles, the sample can be imaged as stained with hematoxylin and eosin (H&E), and also imaged with one or more IHC probes applied and imaged serially to the same sample. This enables a pathologist to review the sample, choose regions for analysis, and visualize structures generally, on the same sample for which component quantization (i.e., biomarker data) are obtained.

Stains that localize in selected tissue regions or materials can be useful in image processing, such as membrane-localizing stains, can be helpful in the automated analyses of IHC imagery of the same sample. For example, images corresponding to histological stains can function as input data for cell segmentation algorithms.

Workflow Efficiency

The enclosed chambers described herein permit a slide-supported sample to be stained and imaged repetitively. Moreover, samples within enclosed chambers can be readily handled without risk to the sample, and readily connected to manual or automated fluidic assemblies and devices.

Substrates with enclosed chambers can be placed into a carrier, so it is convenient to process large numbers of samples efficiently. For example, a carrier with 4 or more such substrates can be connected to an automated fluidic apparatus using a ganged fluidic connection. When labeling is complete, the sample can be disconnected and manually or robotically placed into an automated imaging instrument. When scanning is complete, the batch of substrates can be re-connected to the fluidic apparatus, the labels removed, and the next cycle of labels introduced. This cycle can be repeated, to perform multiplexed IHC analyses with sequential labeling and imaging cycles.

Such workflows can provide several benefits. First, several samples can be processed during each handling step, whether manual or automated. Second, while a given carrier with one group of samples is connected to an automated fluidic assembly, an automated imaging station or device can scan another carrier with another group of samples. Neither the imaging nor the fluidic assembly is idle while the other is active, and maximum utilization is attained.

Further, the sample is not connected to fluidic elements during imaging. This reduces or eliminates the risk of leakage or spills on the imaging components. Still further, the methods described herein can be performed using a variety of imaging stations (e.g., microscopes), since the imaging station does not need to be tightly integrated with the fluidic assembly into a closed system. The second substrate and the fluid in the microfluidic chamber overlying the sample have an optical effect and objectives that have a "focus collar" to compensate for varying amounts of glass or fluid in the optical path and can be used to obtain sample images.

The same sample may be imaged by several different imaging stations or systems within a given imaging cycle, or among different imaging cycles, in an analysis that includes one or more labeling and imaging cycles. For example, one or more sample images can be obtained using specialized microscopy techniques such as confocal, or multiphoton, or super-resolution techniques, to obtain high-resolution images (and high-resolution quantitative information about biomarker expression) at locations where important sample components (targets) are present. During other cycles, the sample can be imaged at lower resolution and/or with different imaging stations or systems, such as a whole-slide scanner.

Guided Labeling and Imaging

The methods described herein can be used to implement guided labeling and imaging workflows. As an example, after an enclosed chamber has been formed around a sample, a histology stain can be applied to the sample, or alternatively, a first labeling and imaging cycle with one or more different types of probes can be performed. Based on the properties of the sample (which can be determined, at least in part, from one or more images of the histology stain and/or one or more labeling agents corresponding to the probes in the sample), a technician or automated controller executing analysis software determines whether to further analyze the sample. In this way, the fitness of each sample can be confirmed based at least partly on its histological and/or IHC response, before further analysis cost and time are expended. Samples that are degraded or unusable can be identified at this point.

In some embodiments, sample information obtained in the foregoing manner is used by a technician or automated controller to select between one of multiple possible staining/labeling and imaging protocols for further sample analysis. Samples from a patient or other subject can be directed along one of several courses of staining/labeling and imaging, depending on what information was initially obtained.

Alternatively, a sample may be processed through one or more cycles of IHC labeling (e.g., labeling and imaging cycles). Unexpected or unpredictable findings obtained in this way may indicate that further IHC measurement of one or more other markers would be valuable in order to gain a fuller understanding of the sample. Additional steps can be performed, including any of the steps described herein such as incubation with one or more primary antibodies, labeling, and imaging, to obtain these measurements.

Following one or more cycles of IHC labeling and imaging, information obtained from sample images can be used to assess the labeling quality and imaging quality obtained. If these are found to be deficient, the sample can be re-processed through one or more of the labeling and imaging cycles. Such assessments may be performed after each labeling and imaging cycle, or at the end of all such cycles, and sample images can be evaluated by a technician or in automated fashion.

Oligonucleotide-Based Sample Labeling

In some embodiments, oligonucleotide-based reagents are used to specifically label and image sample components. One example of such reagents and their associated labeling workflows are the CODEX® reagents available from Akoya Biosciences (Menlo Park, CA). Certain aspects of oligonucleotide-based labeling reagents are described, for example, in U.S. Pat. No. 10,370,698, the entire contents of which are incorporated herein by reference.

Oligonucleotide-based reagents can be used to perform multiple imaging cycles. Each imaging cycle can include the steps of binding one or more probes to a biological sample, obtaining one or more images of the bound probes in the sample, and removing at least a portion of the bound probes from the sample before performing an additional cycle. It should be appreciated that while oligonucleotide-based reagents are well suited for performing multiple imaging cycles, other types of reagents can also be used to perform such cycles, including many of the other types of reagents described herein.

To selectively label one or more components (targets) in a biological sample, the sample can first be incubated with one or more different types of capture agents. Each capture agent includes a binding agent that selectively binds to a sample component (target), and an oligonucleotide that is linked to the binding agent. Typical sample components include antigens and other protein markers, and specific binding agents for these markers include, but are not limited to, antibodies and antibody fragments.

More generally, to target specific antigens, peptides, proteins, or other amino acid-containing species, the binding agent can include an antibody or antibody fragment. The antibody or antibody fragment can include any one of different types of antibody species, including but not limited to, an immunoglobulin G (IgG), an immunoglobulin M (IgM), a polyclonal antibody, a monoclonal antibody, a single-chain fragment variable (scFv) antibody, a nanobody, an antigen-binding fragment (Fab), and a diabody. Antibodies and antibody fragments can be of mouse, rat, rabbit, human, camelid, or goat origin. In some embodiments, the antibody or antibody fragment can be raised against a human, mouse, rat, cow, pig, sheep, monkey, rabbit, fruit fly, frog, nematode or woodchuck antigen. In certain embodiments, the antibody or antibody fragment can be raised against an animal, plant, bacteria, fungus, or protist antigen.

The oligonucleotides that are linked to the binding agents are unique to each type of binding agent. Thus, for example, in a composition that includes three different types of capture agents—each of which selectively binds to a different sample component—each type of capture agent will have the same binding agent linked to the same oligonucleotide. The binding agents among the three types will all be different, and the oligonucleotides of each type of capture agent will be different from those of other types of capture agents.

In some embodiments, the composition that is delivered to the biological sample includes only one type of capture agent. In certain embodiments, however, the composition includes multiple types of capture agents. In particular, during a typical sample analysis workflow, incubation of the sample with capture agents is relatively time consuming. Accordingly, by including multiple types of capture agents (corresponding to multiple different targets or components in the sample) in the composition that is delivered to the sample, many (or even all) incubations can be performed at the same time, significantly increasing the efficiency of analysis.

In some embodiments, the composition delivered to the sample can include 2 or more (e.g., 3 or more, 4 or more, 5 or more, 6 or more, 7 or more, 8 or more, 10 or more, 15 or more, 20 or more, 25 or more, 30 or more, 35 or more, 40 or more, 50 or more, 60 or more, 70 or more, 80 or more, or even more) different types of capture agents.

Each oligonucleotide linked to a capture agent includes a sufficient number of nucleotides so that probes (discussed below) selectively bind to only one type of capture agent. In certain embodiments, the oligonucleotides includes 15 or more (e.g., 20 or more, 25 or more, 30 or more, 35 or more, 40 or more, 45 or more, 50 or more, 55 or more, or even more) nucleic acids.

Following binding of one or more capture agents to the sample, individual types of capture agents are labeled and imaged in one or more labeling, imaging, and label removal cycles. Each such cycle includes three steps. In a first step, the sample is exposed to a composition that includes one or more probes (e.g., by introducing the composition into a chamber, formed as described above, that encloses the sample). Each composition can include one type of probe, or more than one type of probe. Each type of probe selectively binds to only one of the capture agents in the sample.

By including multiple types of probes in the composition, multiplexed sample labeling and imaging can be performed. Each of the different types of probes in the composition binds to a different type of capture agent in the sample at the same time, significantly reducing the time consumed by sample incubation with probes. In some embodiments, the composition can include one or more (e.g., two or more, three or more, four or more, five or more, six or more, seven or more, eight or more, ten or more, or even more) different types of probes.

Each type of probe includes an oligonucleotide linked to a labeling agent. The oligonucleotides of a single probe type are the same, as are the labeling agents. However, the oligonucleotides differ among different probe types, as do the labeling agents. Because each type of probe selectively binds to only one type of capture agent, specific labeling agents are associated with specific capture agents (and therefore, with specific sample components or targets. In this manner, each type of labeling agent acts as a reporter for a different sample component.

Each probe oligonucleotide includes a sufficient number of nucleic acids so that specific binding between pairs of capture agents and probes is achieved. Probe oligonucleotides typically include 15 or more (e.g., 20 or more, 25 or more, 30 or more, 35 or more, 40 or more, 45 or more, 50 or more, or even more) nucleic acids.

To specifically bind to a particular type of capture agent, the oligonucleotide of each type of probe is at least partially complementary to the oligonucleotide of the corresponding capture agent. As used herein, "at least partially complementary" means that no more than 5 mismatches in full complementarity are present between the nucleic acid sequences of the probe oligonucleotide and at least a portion of the capture agent oligonucleotide.

A variety of different labeling agents can be linked to probe oligonucleotides. In some embodiments, for example, the labeling agents include fluorescent moieties have different emission central wavelengths, or emission bandwidths, or both.

Probes can bind to capture agents by hybridization between corresponding oligonucleotides. Hybridization is readily reversed later to remove probes from the sample. Alternatively, other methods for associating probes and capture agents can also be used. In some embodiments, for example, probes can be bound to specific capture agents via ligation or via primer extension reactions, for example.

In the next step of the cycle, the probes bound to the capture agents in the sample are imaged. In particular, fluorescence images corresponding to emission from each of the bound probes are obtained. In some embodiments, fluorescence images that include contributions from substantially only one type of probe can be obtained, e.g., by emission filtering. In certain embodiments, fluorescence images include non-trivial contributions from multiple probes in the sample, and the individual contributions can be separated using techniques such as spectral unmixing.

In the third step of the cycle, the probes are at least partially removed from the sample. In some embodiments, removal of one or more of the probes is complete. In certain embodiments, residual amounts of one or more of the probes remain in the sample. For a terminal cycle (i.e., the final cycle in an analysis workflow), the probes may be left in the sample to facilitate later re-imaging of the sample, e.g., following a period of storage.

In general, removing the probes from the sample involves de-hybridizing the oligonucleotides of the probes and corresponding capture agents. De-hybridization can be performed using various techniques. In some embodiments, for example, de-hybridization can be performed by heating the sample to denature the hybridized oligonucleotides. In certain embodiments, the sample can be exposed to one or more de-hybridizing agents. Examples of such agents include, but are not limited to, chaotropic reagents such as guanidine hydrochloride, guanidine thiocyanate, and urea.

Following removal (or partial removal) of the probes, additional cycles of labeling, imaging, and label removal can be performed to obtain quantitative information about additional components (e.g., biomarkers) in the sample.

The analysis of sample components via oligonucleotide-based reagents can also incorporate TSA-based signal amplification. Methods and reagents for performing TSA amplification with oligonucleotide-based reagents are described, for example, in PCT Patent Application No. PCT/US2020/016667, filed on Feb. 4, 2020, the entire contents of which are incorporated herein by reference.

Automated Systems for Analysis of Single and Multiple Samples

The methods described herein can be implemented in a variety of different analysis systems, including systems that perform some or all of the steps in semi-automated or fully automated fashion. One example of such a system 500 is shown schematically in FIG. 5. System 500 includes a storage unit 502, a labeling station 504, an imaging station 506, and a translation apparatus 510. Each of these components is connected to controller 508, which includes one or more electronic processors that perform control functions associated with controller 508, and can also perform any of the other analysis functions described herein.

Translation apparatus 510 includes a slide handler 512 that attaches to individual slides with samples in enclosed chambers to transport the slides between different locations in the system. An example of a slide with an enclosed chamber and a sample within the chamber is indicated as slide 550 in FIG. 5. Slide handler 512 can be implemented in a number of ways. In some embodiments, for example, slide handler 512 is a grasper and includes one or more arms or fingers that exert pressure on surfaces of slide 550 to lift and transport slide 550. In certain embodiments, slide handler 512 includes a member with one or more suction ports that uses reduced pressure to lift individual slides 550. In certain embodiments, slide handler 512 includes one or more members that are inserted under slides 550 to lift the slides. In general, slide handler 512 can permit both rotational displacements of slides 550 about three orthogonal axes, and translations along three orthogonal axes.

Translation apparatus 510 can also include a track or conveyor 513 that carries individual slides 550 or containers of slides between locations in system 500. In some embodiments, track 513 is a linear track that moves back and forth along a single direction between locations. In certain embodiments, track 513 is a continuous track (e.g., circular, elliptical, or another continuous shape) that circulates among locations in the system.

During operation, controller 508 can transmit appropriate control signals to translation apparatus 510 to retrieve one or more slides 550 from storage unit 502, and to deposit one or more slides into storage unit 502, as discussed above. Further, controller 508 can transmit control signals to translation apparatus 510 to activate labeling station to deliver fluids, reagents, and compositions to the chamber of slide 550, and remove fluids, reagents, compositions (and components thereof) from the chamber of slide 550). Labeling station 504 includes a fluidic apparatus 514 connected to one or more reservoirs 518 and to one or more pumps and/or vacuum sources 519. The fluidic apparatus 514 includes one or more fluid conduits 116 (e.g., syringes, tubes) that can selectively couple to ports 103 and/or 104 of the chamber of slide 550. During operation of the system, controller 508 transmits signals to translation apparatus 510 to position slide 550 within labeling station 504, and transmits signals to the fluidic apparatus 514 to cause one or more of the fluid conduits to couple to one or more ports 103 and/or 104. In this manner, fluids, reagents, and compositions are delivered from reservoirs 518 into the chamber of slide 550, and fluids, reagents, and compositions (and components thereof) are removed from the chamber, so that controller 508 can implement any of the staining and labeling operations described herein in automated fashion. Under the control of controller 508, labeling station 504 can perform any of the sample preparation steps described herein.

Imaging station 506 includes a radiation source 520, an objective lens 524, a beam splitter 522, and an image detector 526. Radiation source 520 can include any one or more of a variety of different sources, including but not limited to LEDs, laser diodes, metal halide sources, incandescent sources, and fluorescent sources. Image detector 526 can include one or more different detector types, including but not limited to CCD detectors and CMOS detectors. During operation of system 500, to obtain an image of a sample within the chamber of slide 550, controller 508 activates translation apparatus 510 to position slide 550 within imaging station 506. Controller 508 then transmits control signals to the components of the imaging station, activating source 520 to deliver illumination radiation to the sample which passes through beam splitter 522 and objective lens 524 and is incident on the sample. Emitted light from the sample passes through objective lens 524, is reflected from beam splitter 522, and is incident on image detector 526, which measures an image of the emitted light.

In FIG. 5, the imaging station is configured to obtain a fluorescence or reflected-light image of the sample. However, it should be appreciated that in some embodiments, detector 526 can be positioned on an opposite side of slide 550 from source 520 to measure a transmitted-light image of the sample. In certain embodiments, imaging station 506 includes multiple detectors for measuring both transmitted- and reflected- or emitted-light (e.g., fluorescence) images of the sample. Under the control of controller 508, imaging station 506 can obtain any of the different types of images corresponds to any of the different types of stains, probes, and labeling agents described herein.

As discussed previously, each of the steps in sample analysis consumes a certain amount of time, and improved efficiency can be obtained by translating multiple slides 550 among multiple locations in system 500, and performing multiple operations. For example, during analysis of multiple slides 550, a first slide containing a first sample in a chamber can be positioned at the labeling station, and the fluidic apparatus can deliver one or more probes to the sample and incubate the sample with the delivered probes. At the same time, a second slide containing a second sample in a chamber can be positioned at the imaging station to obtain one or more images of stains or labeling agents in the sample. A third slide containing a third sample in a chamber can be positioned at the labeling station, where controller 508 activates the one or more pumps and/or vacuum sources to remove fluids, reagents, and/or compositions (and components thereof) from the chamber of the third slide. A fourth slide containing a fourth sample in a chamber can be positioned at the labeling station, where controller 508 activates the fluidic apparatus 514 to deliver a composition that includes one or more primary antibodies into the chamber, and incubates the fourth sample with the antibody composition. Other slides 550 can also be processed—undergoing any of the operations discussed herein—at the same time.

As each slide reaches the end of a set of one or more steps in a preparation or analysis workflow, the slide is transported by translation apparatus 510 to a different location in the system—to a different station, or to a different location within the same station, for example. In this manner, system 500 can simultaneously analyze multiple samples, ensuring that the duty cycles of the components of system 500 remain relatively high, increasing overall throughput of the system for multiple samples relative to simple linear processing of individual samples.

Figure 6:
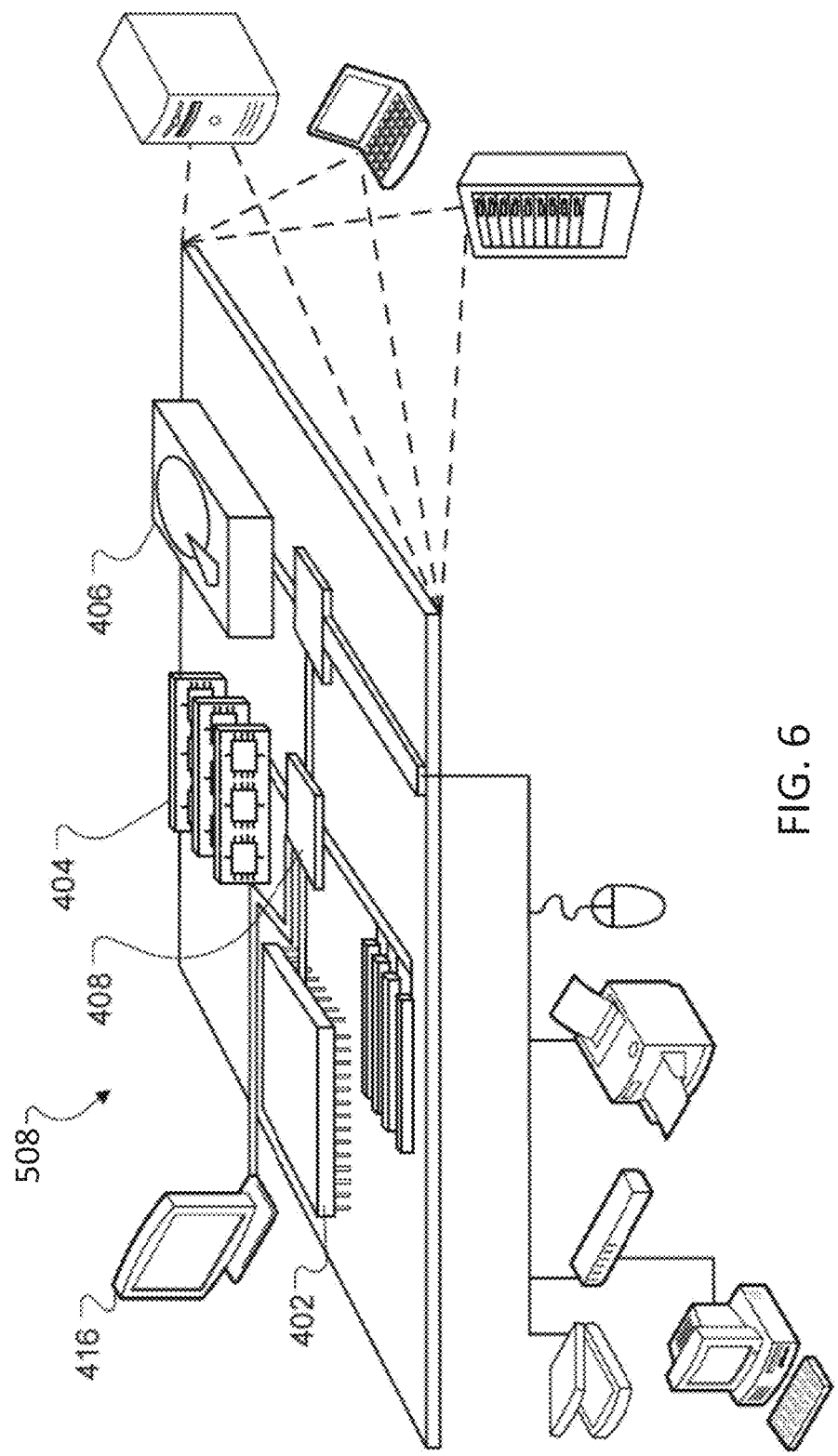
FIG. 6 is a schematic diagram of a controller.

FIG. 6 shows an example of controller 508, which may be used with the systems and methods disclosed herein. Controller 508 can include one or more processors 402, memory 404, a storage device 406 and interfaces 408 for interconnection. The processor(s) 402 can process instructions for execution within the controller, including instructions stored in the memory 404 or on the storage device 406. For example, the instructions can instruct the processor 402 to perform any of the analysis and control steps disclosed herein.

The memory 404 can store executable instructions for processor 402, information about parameters of the system such as excitation and detection wavelengths, and measured spectral image information. The storage device 406 can be a computer-readable medium, such as a floppy disk device, a hard disk device, an optical disk device, or a tape device, a flash memory or other similar solid state memory device, or an array of devices, including devices in a storage area network or other configurations. The storage device 406 can store instructions that can be executed by processor 402 described above, and any of the other information that can be stored by memory 404.

In some embodiments, controller 508 can include a graphics processing unit to display graphical information (e.g., using a GUI or text interface) on an external input/output device, such as display 416. The graphical information can be displayed by a display device (e.g., a CRT (cathode ray tube) or LCD (liquid crystal display) monitor) for displaying any of the information, such as measured and calculated spectra and images, disclosed herein. A user can use input devices (e.g., keyboard, pointing device, touch screen, speech recognition device) to provide input to controller 508.

A user of system 500 can provide a variety of different types of instructions and information to controller 508 via input devices. The instructions and information can include, for example, information about any of the parameters (e.g., stains, labels, probes, reagents, conditions) associated with any of the staining and labeling protocols described herein, calibration information for quantitative analysis of sample images, and instructions following manual analysis of sample images by a technician. Controller 508 can use any of these various types of information to perform the methods and functions described herein. It should also be noted that any of these types of information can be stored (e.g., in storage device 406) and recalled when needed by controller 508.

The methods disclosed herein can be implemented by controller 508 by executing instructions in one or more computer programs that are executable and/or interpretable by the controller 508. These computer programs (also known as programs, software, software applications or code) include machine instructions for a programmable processor, and can be implemented in a high-level procedural and/or object-oriented programming language, and/or in assembly/machine language. For example, computer programs can contain the instructions that can be stored in memory 404, in storage unit 406, and/or on a tangible, computer-readable medium, and executed by processor 402 as described above. As used herein, the term "computer-readable medium" refers to any computer program product, apparatus and/or device (e.g., magnetic discs, optical disks, memory, Programmable Logic Devices (PLDs), ASICs, and electronic circuitry) used to provide machine instructions and/or data to a programmable processor, including a machine-readable medium that receives machine instructions.

EXAMPLES

Example: Multiplexed IHC Labeling and Histochemical Staining

To demonstrate the effectiveness of the methods described herein, an experiment was performed in which a FFPE tissue sample was analyzed via multiplexed IHC labeling and histochemical staining. The sample, mounted on a microscope slide, was warmed for 30 m at a temperature of 55° C. The sample was then equilibrated at room temperature for approximately 10 minutes, and dewaxing was performed. Next, antigen retrieval was performed with tris-ethylenediamine tetraacetic acid (tris-EDTA), followed by a 10 minute cooling period. The sample was then was three times in de-ionized water and incubated for 10 minutes in acetone. After removal from the acetone bath and drying of the sample to remove residual acetone, an enclosed chamber was formed on the microscope slide using the gasket of FIG. 1B, a window, and two port couplers as shown in FIG. 1C.

The sample was then incubated twice, for two minutes each in a buffer solution ("S1") that included EDTA, Dulbecco's phosphate-buffered saline (DPBS), BSA, and $NaN_3$. Afterward, the sample was incubated for 30 minutes in a buffer solution ("S2") that included EDTA, DPBS, BSA, $NaN_3$, NaCl, and $NaH_2PO_3$. Finally, the sample was incubated in a primary antibody composition that included buffer S2, IgG rat-derived N blocker, IgG mouse-derived J block, sheared salmon DNA as an S blocker, a oligo-based G blocker, and 2 μg/mL of a primary antibody mixture that included three different primary antibodies, each linked to three different oligonucleotides, for 3 hours.

After primary antibody incubation, the sample was washed twice in S2 buffer and fixed in a solution of S2 buffer and 1.6% PFA for approximately 4 minutes. Next, the sample was washed three times in DPBS and fixed in methanol for approximately 5 minutes. The sample was then washed three times in DPBS and fixed in a solution of DPBS and BS3 for approximately 6 minutes, and then washed again three times in DPBS.

Finally, the sample was sequentially stained and imaged with DAPI, FITC, and three IHC probes, each of which contained an oligonucleotide that selectively hybridized to one of the primary antibody oligonucleotides and contained a distinct fluorescent labeling agent.

Figure 4A:
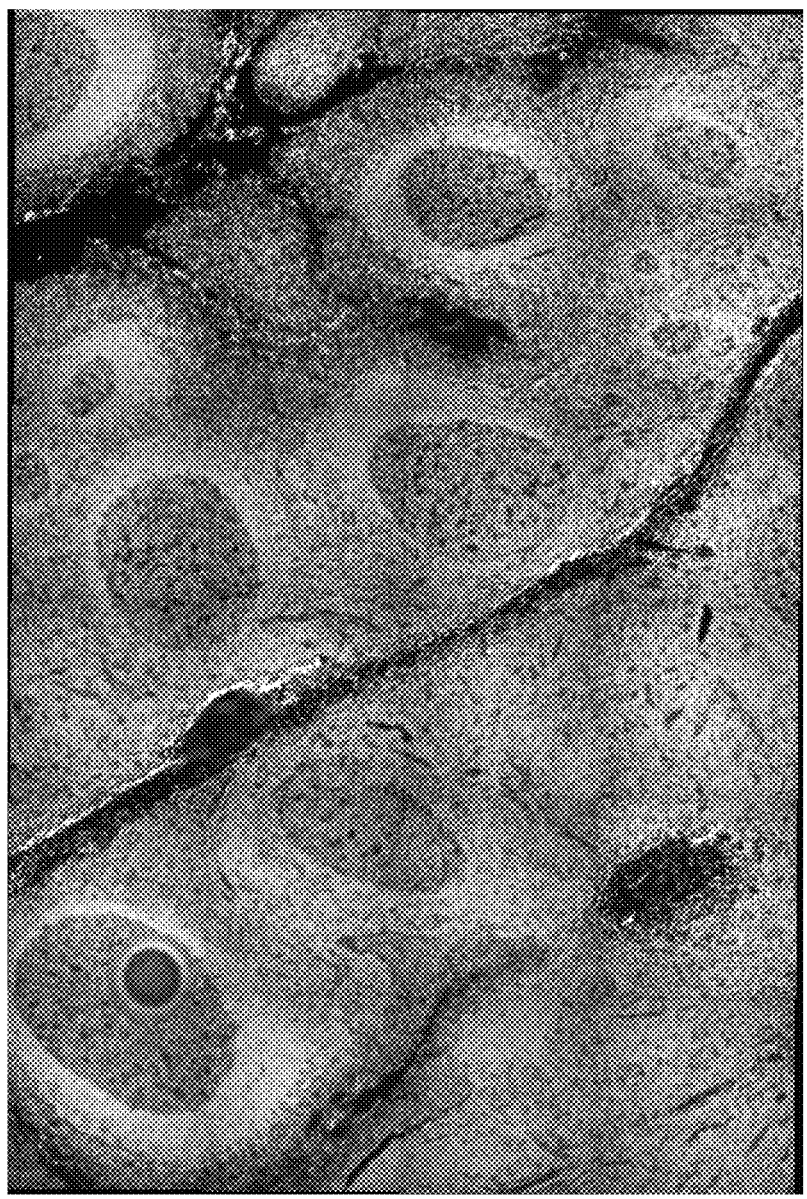
FIG. 4A is an image of a tissue sample stained with DAPI.
Figure 4B:
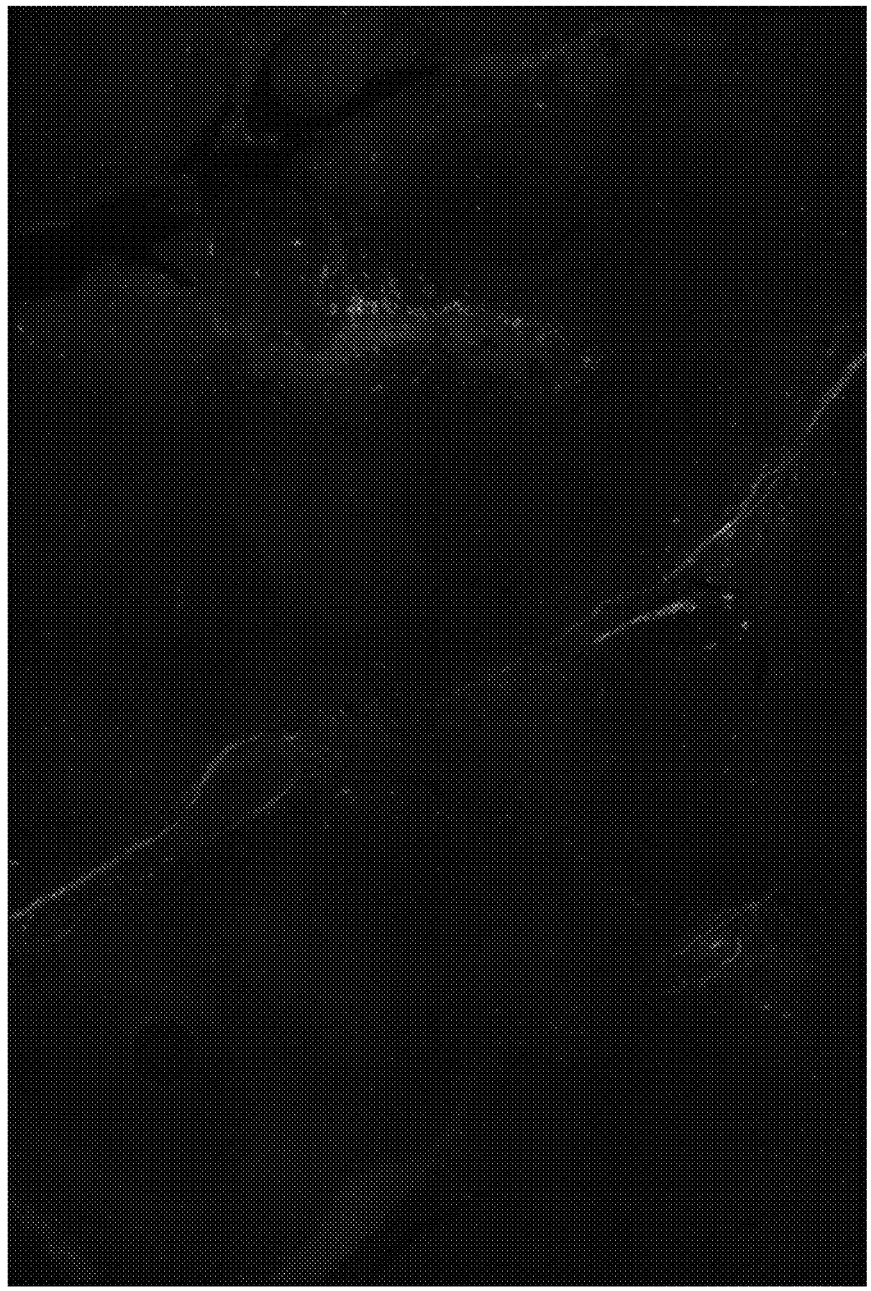
FIG. 4B is an image of a tissue sample stained with FITC.

Images of each of the stains and labels applied to the sample are shown in FIGS. 4A-4E. FIG. 4A is an image showing DAPI distribution within the sample and FIG. 4B is an image showing FITC distribution within the sample.

Figure 4C:
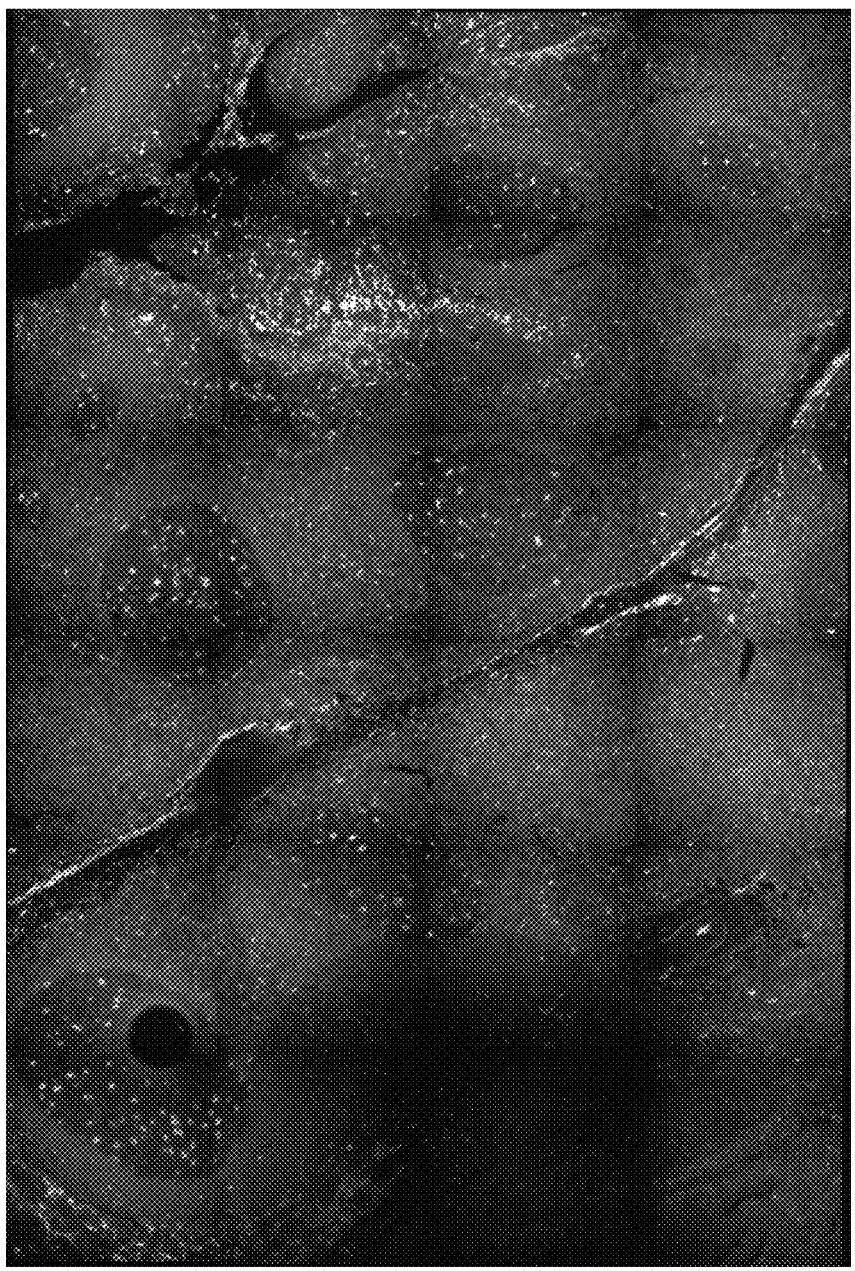
FIG. 4C is an image of a tissue sample labeled with a probe for CD68.
Figure 4D:
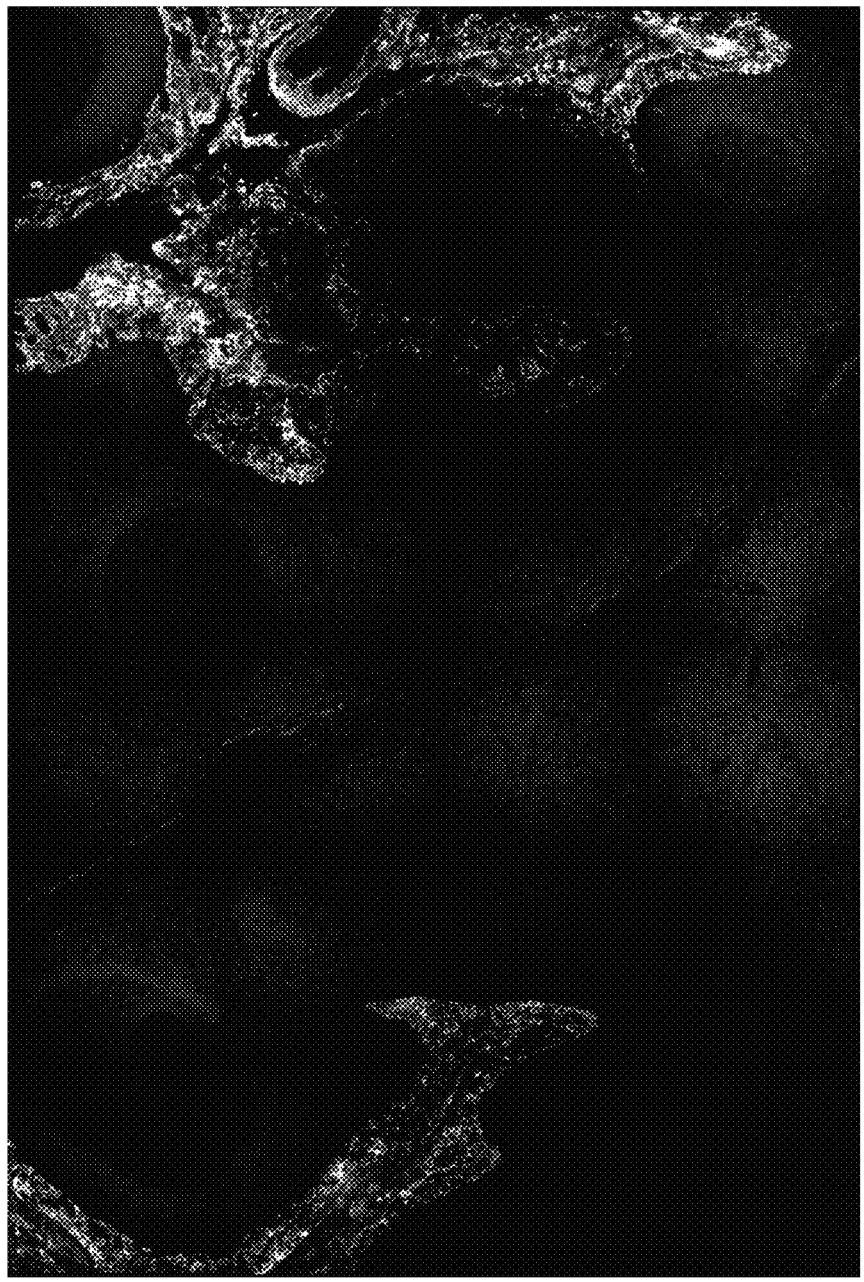
FIG. 4D is an image of a tissue sample labeled with a probe for pancytokeratin.
Figure 4E:
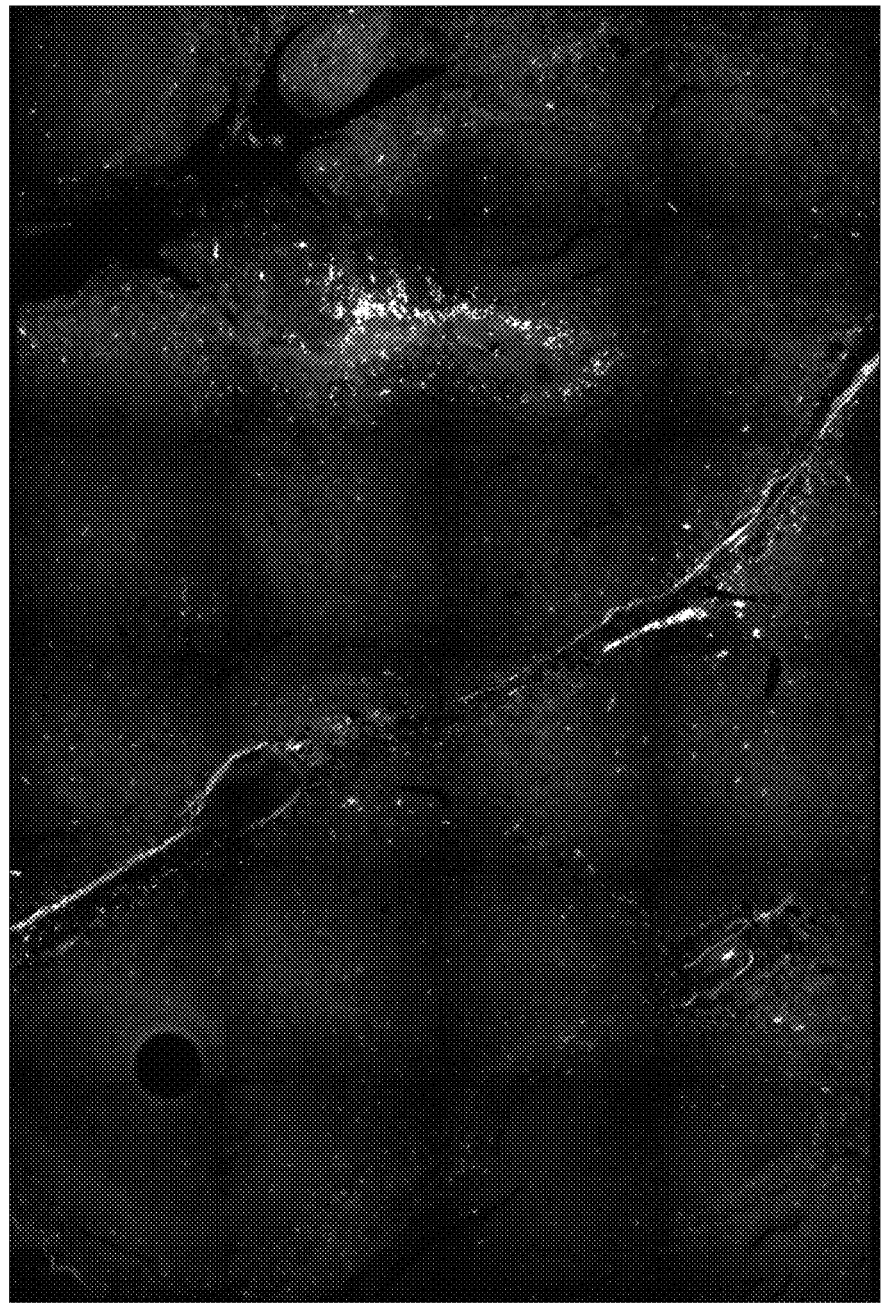
FIG. 4E is an image of a tissue sample labeled with a probe for E-cadherin.

FIGS. 4C-4E show the distributions of CD68 (corresponding fluorescent label Cy5), pancytokeratin (corresponding fluorescent label AlexaFluor® 750), and E-cadherin (corresponding fluorescent label Atto 550). Each of these markers is clearly visible in the corresponding images.

OTHER EMBODIMENTS

While this disclosure describes specific implementations, these should not be construed as limitations on the scope of the disclosure, but rather as descriptions of features in certain embodiments. Features that are described in the context of separate embodiments can also generally be implemented in combination in a single embodiment. Conversely, various features that are described in the context of a single embodiment can also be implemented in multiple embodiments separately or in any suitable sub-combination. Moreover, although features may be described above as present in certain combinations and even initially claimed as such, one or more features from a claimed combination can generally be excised from the combination, and the claimed combination may be directed to a sub-combination or variation of a sub-combination.

In addition to the embodiments expressly disclosed herein, it will be understood that various modifications to the embodiments described may be made without departing from the spirit and scope of the disclosure. Accordingly, other embodiments are within the scope of the following claims.

What is claimed is:

1. A method for analyzing a biological sample, the method comprising:
   obtaining a biological sample mounted on a first substrate;
   affixing a second substrate to the first substrate to form an enclosed chamber on the first substrate with the biological sample positioned within an interior volume of the enclosed chamber, wherein the second substrate comprises a first port formed by a first aperture extending through a thickness of the second substrate and a second port formed by a second aperture extending through the thickness of the second substrate;
   introducing a composition into the interior volume through the first port, wherein the composition comprises multiple different types of capture agents, each of the different types of capture agents comprising a different type of binding agent that selectively binds to a different sample component and an oligonucleotide linked to the binding agent that is specific to each different type of binding agent, wherein each of the different types of capture agents is bound to the biological sample by introducing the different types of capture agents at the same time into the interior volume of the enclosed chamber; and
   performing multiple imaging cycles, wherein each imaging cycle comprises:
   (a) binding a probe to the biological sample;
   (b) obtaining an image of the bound probe in the biological sample; and
   (c) removing at least a portion of the probe from the biological sample,
   wherein a thickness of the interior volume between the first and second substrates is 250 micrometers or less.

2. The method of claim 1, wherein the first substrate is formed of a substantially transparent material.

3. The method of claim 1, wherein the second substrate comprises a window.

4. The method of claim 1, further comprising positioning a gasket between the first and second substrates, wherein the gasket is formed of an adhesive material.

5. The method of claim 1, further comprising, prior to affixing the second substrate to the first substrate:
   incubating the biological sample in acetone;
   removing residual acetone from the biological sample; and
   affixing the second substrate to the first substrate following the removal of residual acetone.

6. The method of claim 1, further comprising, prior to performing the multiple imaging cycles, applying a stain to the biological sample.

7. The method of claim 1, wherein the interior volume is $0.20$ cm$^3$ or less.

8. The method of claim 1, wherein during each imaging cycle, the probe is bound to the biological sample by introducing a composition comprising the probe through the first port, and removing components of the composition through the second port.

9. The method of claim 1, wherein binding the probe to the biological sample comprises binding one or more different types of probes to the biological sample, wherein each different type of probe comprises a different type of oligonucleotide linked to a labeling agent that is specific to each different type of oligonucleotide.

10. The method of claim 9, wherein the one or more different types of probes are bound to the biological sample at the same time by introducing a composition comprising the one or more different types of probes into the interior volume of the enclosed chamber, and wherein the one or more different types of probes bind to corresponding different types of capture agents in the biological sample.

11. A method for analyzing a biological sample, the method comprising:
   obtaining a biological sample mounted on a first substrate;
   affixing a second substrate to the first substrate to form an enclosed chamber on the first substrate with the biological sample positioned within an interior volume of the enclosed chamber, wherein the second substrate comprises a first port formed by a first aperture extending through a thickness of the second substrate and a second port formed by a second aperture extending through the thickness of the second substrate;
   introducing a composition comprising multiple different types of capture agents through the first port, each of the different types of capture agents comprising a different type of binding agent that selectively binds to a different sample component and an oligonucleotide linked to the binding agent that is specific to each different type of binding agent; and
   performing multiple imaging cycles, wherein each imaging cycle comprises:
   (a) binding a probe to the biological sample;
   (b) obtaining an image of the bound probe in the biological sample; and
   (c) removing at least a portion of the probe from the biological sample,
   wherein the first and second substrates are substantially transparent; and
   wherein an imaging window formed by the first and second substrates has a field of view of at least 500 mm$^2$.

12. The method of claim 11, wherein the first substrate comprises a microscope slide.

13. The method of claim 11, wherein the second substrate comprises a window.

14. The method of claim 11, further comprising positioning a gasket between the first and second substrates, wherein the gasket is formed of an adhesive material.

15. The method of claim 11, further comprising, prior to affixing the second substrate to the first substrate:
incubating the biological sample in acetone;
removing residual acetone from the biological sample; and
affixing the second substrate to the first substrate following the removal of residual acetone.

16. The method of claim 11, further comprising, prior to performing the multiple imaging cycles, applying a stain to the biological sample.

17. The method of claim 11, wherein a minimum distance between the first and second ports measured in a plane of the second substrate is 20 mm or more.

18. The method of claim 11, wherein during each imaging cycle, the probe is bound to the biological sample by introducing a composition comprising the probe through the first port, and removing components of the composition through the second port.

19. The method of claim 11, wherein each of the different types of capture agents is bound to the biological sample by introducing the composition comprising each of the different types of capture agents at the same time into the interior volume of the enclosed chamber.

20. The method of claim 16, wherein binding the probe to the biological sample comprises binding one or more different types of probes to the biological sample, wherein each different type of probe comprises a different type of oligonucleotide linked to a labeling agent that is specific to each different type of oligonucleotide.

21. The method of claim 16, further comprising, prior to introducing the composition into the interior volume of the enclosed chamber, connecting a port coupler to at least one of the first and second ports.

22. A method for analyzing a biological sample, the method comprising:
obtaining a biological sample mounted on a first substrate;
affixing a second substrate to the first substrate to form an enclosed chamber on the first substrate with the biological sample positioned within an interior volume of the enclosed chamber, wherein the second substrate comprises a first port formed by a first aperture extending through a thickness of the second substrate and a second port formed by a second aperture extending through the thickness of the second substrate, and wherein compositions are introduced into the interior volume through the first port;
prior to introducing a composition into the interior volume of the enclosed chamber, connecting a port coupler to at least one of the first and second ports; and
performing multiple imaging cycles, wherein each imaging cycle comprises:
(a) binding a probe to the biological sample;
(b) obtaining an image of the bound probe in the biological sample; and
(c) removing at least a portion of the probe from the biological sample,
wherein the first and second substrates are substantially transparent.

23. The method of claim 22, wherein the first substrate is formed of a substantially transparent material.

24. The method of claim 22, wherein the second substrate comprises a window.

25. The method of claim 22, further comprising positioning a gasket between the first and second substrates, wherein the gasket is formed of an adhesive material.

26. The method of claim 22, further comprising, prior to affixing the second substrate to the first substrate:
incubating the biological sample in acetone;
removing residual acetone from the biological sample; and
affixing the second substrate to the first substrate following the removal of residual acetone.

27. The method of claim 22, further comprising, prior to performing the multiple imaging cycles, applying a stain to the biological sample.

28. The method of claim 22, wherein during each imaging cycle, the probe is bound to the biological sample by introducing a composition comprising the probe through the first port, and removing components of the composition through the second port.

29. The method of claim 22, further comprising, prior to performing the multiple imaging cycles, binding a capture agent to the biological sample by introducing a composition comprising the capture agent through the first port.

30. The method of claim 29, wherein the capture agent comprises a binding agent that selectively binds to a sample component, and an oligonucleotide that is linked to the binding agent.

31. The method of claim 30, wherein the composition comprises multiple different types of capture agents, each of the different types of capture agents comprising a different type of binding agent that selectively binds to a different sample component, and an oligonucleotide that is specific to each different type of binding agent.

32. The method of claim 31, wherein each of the different types of capture agents is bound to the biological sample by introducing the composition comprising each of the different types of capture agents at the same time into the interior volume of the enclosed chamber.

33. The method of claim 22, wherein binding the probe to the biological sample comprises binding one or more different types of probes to the biological sample, wherein each different type of probe comprises a different type of oligonucleotide linked to a labeling agent that is specific to each different type of oligonucleotide.

34. The method of claim 33, wherein the one or more different types of probes are bound to the biological sample at the same time by introducing a composition comprising the one or more different types of probes into the interior volume of the enclosed chamber, and wherein the one or more different types of probes bind to corresponding different types of capture agents in the biological sample.

35. The method of claim 22, wherein the interior volume is 0.20 cm$^3$ or less.

* * * * *